US010471016B2

(12) United States Patent
Mooney et al.

(10) Patent No.: US 10,471,016 B2
(45) Date of Patent: Nov. 12, 2019

(54) MICROPARTICLES, METHODS FOR THEIR PREPARATION AND USE

(71) Applicant: President and Fellows of Harvard College, Cambridge, MA (US)

(72) Inventors: David J. Mooney, Sudbury, MA (US); David A. Weitz, Bolton, MA (US); Stefanie Utech, Erlangen (DE); Radivoje Prodanovich, Belgrade (RS); Esther Amstad, Lausanne (CH); Raluca Ostafe, Aachen (DE); Angelo S. Mao, Somerville, MA (US); Connie Chang Wilking, Bozeman, MT (US); Huanan Wang, Dalian (CN)

(73) Assignee: President and Fellows of Harvard College, Cambridge, MA (US)

( * ) Notice: Subject to any disclaimer, the term of this patent is extended or adjusted under 35 U.S.C. 154(b) by 0 days.

(21) Appl. No.: 15/915,686

(22) Filed: Mar. 8, 2018

(65) Prior Publication Data

US 2018/0214385 A1     Aug. 2, 2018

Related U.S. Application Data

(62) Division of application No. 15/035,167, filed as application No. PCT/US2014/063846 on Nov. 4, 2014.

(60) Provisional application No. 61/901,949, filed on Nov. 8, 2013.

(51) Int. Cl.
*A61K 9/50* (2006.01)
*A61K 9/16* (2006.01)
*A61K 35/00* (2006.01)

(52) U.S. Cl.
CPC .......... *A61K 9/5036* (2013.01); *A61K 9/1652* (2013.01); *A61K 9/5089* (2013.01); *A61K 35/00* (2013.01)

(58) Field of Classification Search
CPC ..... A61K 9/5036; A61K 9/1962; A61K 35/00
See application file for complete search history.

(56) References Cited

U.S. PATENT DOCUMENTS

| | | | |
|---|---|---|---|
| 4,732,930 A | 3/1988 | Tanaka et al. |
| 4,743,507 A | 5/1988 | Franses et al. |
| 4,996,265 A | 2/1991 | Okubo et al. |
| 5,055,390 A | 10/1991 | Weaver et al. |
| 5,100,933 A | 3/1992 | Tanaka et al. |
| 5,120,349 A | 6/1992 | Stewart et al. |
| 5,149,625 A | 9/1992 | Church et al. |
| 5,202,231 A | 4/1993 | Drmanac et al. |

(Continued)

FOREIGN PATENT DOCUMENTS

| | | |
|---|---|---|
| EP | 0 249 007 A2 | 12/1987 |
| EP | 0 272 659 A2 | 6/1988 |

(Continued)

OTHER PUBLICATIONS

U.S. Appl. No. 15/670,977, filed Aug. 7, 2017, Weitz et al.

(Continued)

*Primary Examiner* — Carlos A Azpuru
(74) *Attorney, Agent, or Firm* — Wolf, Greenfield & Sacks, P.C.

(57) ABSTRACT

The invention relates to microparticles comprising a crosslinked gel and methods for making and using same.

16 Claims, 7 Drawing Sheets

(56) References Cited

U.S. PATENT DOCUMENTS

| | | |
|---|---|---|
| 5,216,096 A | 6/1993 | Hattori et al. |
| 5,326,692 A | 7/1994 | Brinkley et al. |
| 5,436,130 A | 7/1995 | Mathies et al. |
| 5,500,223 A | 3/1996 | Behan et al. |
| 5,512,131 A | 4/1996 | Kumar et al. |
| 5,695,940 A | 12/1997 | Drmanac et al. |
| 5,736,330 A | 4/1998 | Fulton |
| 5,834,252 A | 11/1998 | Stemmer et al. |
| 5,849,055 A | 12/1998 | Arai et al. |
| 5,851,769 A | 12/1998 | Gray et al. |
| 6,046,003 A | 4/2000 | Mandecki |
| 6,051,377 A | 4/2000 | Mandecki |
| 6,057,107 A | 5/2000 | Fulton |
| 6,103,537 A | 8/2000 | Ullman et al. |
| 6,297,006 B1 | 10/2001 | Drmanac et al. |
| 6,297,017 B1 | 10/2001 | Schmidt et al. |
| 6,355,198 B1 | 3/2002 | Kim et al. |
| 6,361,950 B1 | 3/2002 | Mandecki |
| 6,380,297 B1 | 4/2002 | Zion et al. |
| 6,432,360 B1 | 8/2002 | Church |
| 6,485,944 B1 | 11/2002 | Church et al. |
| 6,500,447 B1 * | 12/2002 | Dexter .................. A01N 25/28 264/4.1 |
| 6,511,803 B1 | 1/2003 | Church et al. |
| 6,524,456 B1 | 2/2003 | Ramsey et al. |
| 6,586,176 B1 | 7/2003 | Trnovsky et al. |
| 6,632,606 B1 | 10/2003 | Ullman et al. |
| 6,670,133 B2 | 12/2003 | Knapp et al. |
| 6,767,731 B2 | 7/2004 | Hannah |
| 6,800,298 B1 | 10/2004 | Burdick et al. |
| 6,806,058 B2 | 10/2004 | Jesperson et al. |
| 6,913,935 B1 | 7/2005 | Thomas |
| 6,929,859 B2 | 8/2005 | Chandler et al. |
| 7,041,481 B2 | 5/2006 | Anderson et al. |
| 7,268,167 B2 | 9/2007 | Higuchi et al. |
| 7,425,431 B2 | 9/2008 | Church et al. |
| 7,536,928 B2 | 5/2009 | Kazuno |
| 7,604,938 B2 | 10/2009 | Takahashi et al. |
| 7,638,276 B2 | 12/2009 | Griffiths et al. |
| 7,708,949 B2 | 5/2010 | Stone et al. |
| 7,776,927 B2 | 8/2010 | Chu et al. |
| RE41,780 E | 9/2010 | Anderson et al. |
| 7,799,553 B2 | 9/2010 | Mathies et al. |
| 7,968,287 B2 | 6/2011 | Griffiths et al. |
| 8,252,539 B2 | 8/2012 | Quake et al. |
| 8,273,573 B2 | 9/2012 | Ismagilov et al. |
| 8,278,071 B2 | 10/2012 | Brown et al. |
| 8,329,407 B2 | 12/2012 | Ismagilov et al. |
| 8,748,094 B2 | 6/2014 | Weitz et al. |
| 8,748,102 B2 | 6/2014 | Berka et al. |
| 8,765,380 B2 | 7/2014 | Berka et al. |
| 8,871,444 B2 | 10/2014 | Griffiths et al. |
| 9,017,948 B2 | 4/2015 | Agresti et al. |
| 9,029,085 B2 | 5/2015 | Agresti et al. |
| 9,039,273 B2 | 5/2015 | Weitz et al. |
| 9,068,210 B2 | 6/2015 | Agresti et al. |
| 9,816,121 B2 | 6/2017 | Agresti et al. |
| 9,718,044 B2 | 8/2017 | Wesner et al. |
| 9,850,526 B2 | 12/2017 | Agresti et al. |
| 10,221,437 B2 | 3/2019 | Weitz et al. |
| 2001/0020588 A1 | 9/2001 | Adourian et al. |
| 2001/0044109 A1 | 11/2001 | Mandecki |
| 2002/0034737 A1 | 3/2002 | Drmanac |
| 2002/0034747 A1 | 3/2002 | Bruchez et al. |
| 2002/0051992 A1 | 5/2002 | Bridgham et al. |
| 2002/0092767 A1 | 7/2002 | Bjornson et al. |
| 2002/0179849 A1 | 12/2002 | Maher et al. |
| 2003/0008285 A1 | 1/2003 | Fischer |
| 2003/0008323 A1 | 1/2003 | Ravkin et al. |
| 2003/0028981 A1 | 2/2003 | Chandler et al. |
| 2003/0039978 A1 | 2/2003 | Hannah |
| 2003/0044777 A1 | 3/2003 | Beattie |
| 2003/0044836 A1 | 3/2003 | Levine et al. |
| 2003/0099954 A1 | 5/2003 | Miltenyi et al. |
| 2003/0104466 A1 | 6/2003 | Knapp et al. |
| 2003/0108897 A1 | 6/2003 | Drmanac |
| 2003/0170698 A1 | 9/2003 | Gascoyne et al. |
| 2003/0182068 A1 | 9/2003 | Battersby et al. |
| 2003/0207260 A1 | 11/2003 | Trnovsky et al. |
| 2003/0215862 A1 | 11/2003 | Parce et al. |
| 2004/0063138 A1 | 4/2004 | McGinnis et al. |
| 2004/0096515 A1 | 5/2004 | Bausch et al. |
| 2004/0132122 A1 | 7/2004 | Banerjee et al. |
| 2004/0253613 A1 | 12/2004 | Taylor et al. |
| 2005/0019839 A1 | 1/2005 | Jesperson et al. |
| 2005/0042625 A1 | 2/2005 | Schmidt et al. |
| 2005/0123614 A1 | 6/2005 | Kim et al. |
| 2005/0136486 A1 | 6/2005 | Haushalter |
| 2005/0172476 A1 | 8/2005 | Stone et al. |
| 2005/0181379 A1 | 8/2005 | Su et al. |
| 2005/0221339 A1 | 10/2005 | Griffiths et al. |
| 2005/0244850 A1 | 11/2005 | Huang et al. |
| 2005/0287572 A1 | 12/2005 | Mathies et al. |
| 2006/0020371 A1 | 1/2006 | Ham et al. |
| 2006/0073487 A1 | 4/2006 | Oliver et al. |
| 2006/0078888 A1 | 4/2006 | Griffiths et al. |
| 2006/0078893 A1 | 4/2006 | Griffiths et al. |
| 2006/0153924 A1 | 7/2006 | Griffiths et al. |
| 2006/0163385 A1 | 7/2006 | Link et al. |
| 2006/0240506 A1 | 10/2006 | Kushmaro et al. |
| 2006/0257893 A1 | 11/2006 | Takahashi et al. |
| 2006/0292583 A1 | 12/2006 | Schneider et al. |
| 2007/0003442 A1 | 1/2007 | Link et al. |
| 2007/0020617 A1 | 1/2007 | Trnovsky et al. |
| 2007/0054119 A1 | 3/2007 | Garstecki et al. |
| 2007/0092914 A1 | 4/2007 | Griffiths et al. |
| 2007/0172827 A1 | 7/2007 | Murakami |
| 2007/0172873 A1 | 7/2007 | Brenner et al. |
| 2007/0195127 A1 | 8/2007 | Ahn et al. |
| 2007/0228588 A1 | 10/2007 | Noritomi et al. |
| 2007/0264320 A1 | 11/2007 | Lee et al. |
| 2008/0003142 A1 | 1/2008 | Link et al. |
| 2008/0004436 A1 | 1/2008 | Tawfik et al. |
| 2008/0014589 A1 | 1/2008 | Link et al. |
| 2009/0012187 A1 | 1/2009 | Chu et al. |
| 2009/0035770 A1 | 2/2009 | Mathies et al. |
| 2009/0068170 A1 | 3/2009 | Weitz et al. |
| 2009/0131543 A1 | 5/2009 | Weitz et al. |
| 2009/0134027 A1 | 5/2009 | Jary |
| 2009/0191276 A1 | 7/2009 | Kim et al. |
| 2009/0197772 A1 | 8/2009 | Griffiths et al. |
| 2009/0205829 A1 | 8/2009 | Sullivan et al. |
| 2009/0286687 A1 | 11/2009 | Dressman et al. |
| 2010/0022414 A1 | 1/2010 | Link et al. |
| 2010/0130369 A1 | 5/2010 | Shenderov et al. |
| 2010/0136544 A1 | 6/2010 | Agresti et al. |
| 2010/0137163 A1 | 6/2010 | Link et al. |
| 2010/0173394 A1 | 7/2010 | Colston, Jr. et al. |
| 2010/0210479 A1 | 8/2010 | Griffiths et al. |
| 2010/0213628 A1 | 8/2010 | Bausch et al. |
| 2010/0273219 A1 | 10/2010 | May et al. |
| 2011/0033854 A1 | 2/2011 | Drmanac et al. |
| 2011/0086780 A1 | 4/2011 | Colston et al. |
| 2011/0092392 A1 | 4/2011 | Colston et al. |
| 2011/0160078 A1 | 6/2011 | Fodor et al. |
| 2011/0218123 A1 | 9/2011 | Weitz et al. |
| 2011/0229545 A1 | 9/2011 | Shum et al. |
| 2011/0267457 A1 | 11/2011 | Weitz et al. |
| 2011/0305761 A1 | 12/2011 | Shum et al. |
| 2012/0003321 A1 | 1/2012 | Peng et al. |
| 2012/0010107 A1 | 1/2012 | Griffiths et al. |
| 2012/0015382 A1 | 1/2012 | Weitz et al. |
| 2012/0015822 A1 | 1/2012 | Weitz et al. |
| 2012/0076860 A1 | 3/2012 | Trout et al. |
| 2012/0135407 A1 | 5/2012 | Slatter |
| 2012/0190032 A1 | 7/2012 | Ness et al. |
| 2012/0199226 A1 | 8/2012 | Weitz et al. |
| 2012/0211084 A1 | 8/2012 | Weitz et al. |
| 2012/0220494 A1 | 8/2012 | Samuels et al. |
| 2012/0220497 A1 | 8/2012 | Jacobson et al. |
| 2012/0222748 A1 | 9/2012 | Weitz et al. |
| 2013/0004522 A1 | 1/2013 | Dvir et al. |
| 2013/0046030 A1 | 2/2013 | Rotem et al. |

(56) References Cited

U.S. PATENT DOCUMENTS

| | | | |
|---|---|---|---|
| 2013/0064862 A1* | 3/2013 | Weitz | A01N 25/28 424/400 |
| 2013/0079231 A1 | 3/2013 | Pushkarev et al. | |
| 2013/0109575 A1 | 5/2013 | Kleinschmidt et al. | |
| 2013/0157899 A1 | 6/2013 | Adler et al. | |
| 2013/0210639 A1 | 8/2013 | Link et al. | |
| 2013/0274117 A1 | 10/2013 | Church et al. | |
| 2014/0065234 A1 | 3/2014 | Shum et al. | |
| 2014/0155295 A1 | 6/2014 | Hindson et al. | |
| 2014/0199730 A1 | 7/2014 | Agresti et al. | |
| 2014/0199731 A1 | 7/2014 | Agresti et al. | |
| 2014/0220350 A1 | 8/2014 | Kim et al. | |
| 2014/0227684 A1 | 8/2014 | Hindson et al. | |
| 2014/0235506 A1 | 8/2014 | Hindson et al. | |
| 2014/0303039 A1 | 10/2014 | Weitz et al. | |
| 2014/0378349 A1 | 12/2014 | Hindson et al. | |
| 2015/0005200 A1 | 1/2015 | Hindson et al. | |
| 2015/0314292 A1 | 11/2015 | Weitz et al. | |
| 2015/0336068 A1 | 11/2015 | Weitz et al. | |
| 2015/0336069 A1 | 11/2015 | Weitz et al. | |
| 2015/0336070 A1 | 11/2015 | Weitz et al. | |
| 2015/0336071 A1 | 11/2015 | Weitz et al. | |
| 2015/0336072 A1 | 11/2015 | Weitz et al. | |
| 2015/0337371 A1 | 11/2015 | Weitz et al. | |
| 2015/0353999 A1 | 12/2015 | Agresti et al. | |
| 2016/0279068 A1 | 9/2016 | Utech et al. | |
| 2017/0183701 A1 | 6/2017 | Agresti et al. | |
| 2017/0224849 A1 | 8/2017 | Carroll et al. | |
| 2017/0319443 A1 | 12/2017 | Weitz et al. | |
| 2018/0023109 A1 | 1/2018 | Weitz et al. | |
| 2018/0119212 A1 | 5/2018 | Weitz et al. | |
| 2018/0171373 A1 | 6/2018 | Weitz et al. | |
| 2018/0296488 A1 | 10/2018 | Weitz et al. | |

FOREIGN PATENT DOCUMENTS

| | | |
|---|---|---|
| EP | 0 478 326 A1 | 4/1992 |
| EP | 1 019 496 B1 | 9/2004 |
| EP | 1 482 036 B1 | 10/2007 |
| EP | 1 594 980 B1 | 11/2009 |
| EP | 1 967 592 B1 | 4/2010 |
| EP | 2 258 846 A2 | 12/2010 |
| EP | 2 145 955 B1 | 2/2012 |
| EP | 1 905 828 B1 | 8/2012 |
| EP | 1 908 832 B1 | 12/2012 |
| EP | 2 540 389 A1 | 1/2013 |
| JP | S59-049832 A2 | 3/1984 |
| JP | 2004-361291 A | 12/2004 |
| JP | 2006-507921 A | 3/2006 |
| JP | 2006-289250 A | 10/2006 |
| JP | 2007-268350 A | 10/2007 |
| JP | 2007-298327 A | 11/2007 |
| JP | 2009-208074 A2 | 9/2009 |
| KR | 2014/0107381 A | 9/2014 |
| WO | WO 95/09613 A1 | 4/1995 |
| WO | WO 96/29629 A2 | 9/1996 |
| WO | WO 96/41011 A1 | 12/1996 |
| WO | WO 99/09217 A1 | 2/1999 |
| WO | WO 99/52708 A1 | 10/1999 |
| WO | WO 00/08212 A1 | 2/2000 |
| WO | WO 00/26412 A1 | 5/2000 |
| WO | WO 01/14589 A2 | 3/2001 |
| WO | WO 01/85138 A2 | 11/2001 |
| WO | WO 01/89787 A2 | 11/2001 |
| WO | WO 02/31203 A2 | 4/2002 |
| WO | WO 02/047665 A2 | 6/2002 |
| WO | WO 02/086148 A1 | 10/2002 |
| WO | WO 03/028653 A2 | 4/2003 |
| WO | WO 2004/002627 A2 | 1/2004 |
| WO | WO 2004/091763 A2 | 10/2004 |
| WO | WO 2004/102204 A1 | 11/2004 |
| WO | WO 2004/103565 A2 | 12/2004 |
| WO | WO 2004/105734 A1 | 12/2004 |
| WO | WO 2005/021151 A1 | 3/2005 |
| WO | WO 2005/040406 A1 | 5/2005 |
| WO | WO 2005/041884 A2 | 5/2005 |
| WO | WO 2005/049787 A2 | 6/2005 |
| WO | WO 2005/082098 A2 | 9/2005 |
| WO | WO 2005/084210 A2 | 9/2005 |
| WO | WO 2005/103106 A1 | 11/2005 |
| WO | WO 2006/078841 A1 | 7/2006 |
| WO | WO 2006/096571 A2 | 9/2006 |
| WO | WO 2007/001448 A2 | 1/2007 |
| WO | WO 2007/002490 A2 | 1/2007 |
| WO | WO 2007/012638 A2 | 2/2007 |
| WO | WO 2007/024840 A2 | 3/2007 |
| WO | WO 2007/081385 A2 | 7/2007 |
| WO | WO 2007/081387 A1 | 7/2007 |
| WO | WO 2007/089541 A2 | 8/2007 |
| WO | WO 2007/114794 A1 | 10/2007 |
| WO | WO 2007/121489 A2 | 10/2007 |
| WO | WO 2007/133710 A2 | 11/2007 |
| WO | WO 2007/133807 A2 | 11/2007 |
| WO | WO 2007/138178 A2 | 12/2007 |
| WO | WO 2007/139766 A2 | 12/2007 |
| WO | WO 2007/140015 A2 | 12/2007 |
| WO | WO 2007/149432 A2 | 12/2007 |
| WO | WO 2008/021123 A1 | 2/2008 |
| WO | WO 2008/058297 A2 | 5/2008 |
| WO | WO 2008/091792 A2 | 7/2008 |
| WO | WO 2008/102057 A1 | 8/2008 |
| WO | WO 2008/109176 A2 | 9/2008 |
| WO | WO 2008/121342 A2 | 10/2008 |
| WO | WO 2008/134153 A1 | 11/2008 |
| WO | WO 2009/005680 A1 | 1/2009 |
| WO | WO 2009/011808 A1 | 1/2009 |
| WO | WO 2009/085215 A1 | 7/2009 |
| WO | WO 2009/120254 A1 | 10/2009 |
| WO | WO 2009/148598 A1 | 12/2009 |
| WO | WO 2010/104604 A1 | 9/2010 |
| WO | WO 2010/151776 A2 | 12/2010 |
| WO | WO 2011/028760 A2 | 3/2011 |
| WO | WO 2011/028764 A2 | 3/2011 |
| WO | WO 2011/056546 A1 | 5/2011 |
| WO | WO 2011/116154 A2 | 9/2011 |
| WO | WO 2012/048341 A1 | 4/2012 |
| WO | WO 2012/156744 A2 | 11/2012 |
| WO | WO 2012/162296 A2 | 11/2012 |
| WO | WO 2013/006661 A2 | 1/2013 |
| WO | WO 2013/032709 A2 | 3/2013 |
| WO | WO 2013/083760 A2 | 6/2013 |
| WO | WO 2013/177220 A1 | 11/2013 |
| WO | WO 2015/069634 A1 | 5/2015 |
| WO | WO 2015/160919 A1 | 10/2015 |
| WO | WO 2016/085739 | 6/2016 |
| WO | WO 2017/066231 | 4/2017 |

OTHER PUBLICATIONS

U.S. Appl. No. 15/792,218, filed Oct. 24, 2017, Weitz et al.
U.S. Appl. No. 15/884,215, filed Jan. 30, 2018, Weitz et al.
U.S. Appl. No. 13/119,470, filed May 4, 2011, Weitz et al.
U.S. Appl. No. 14/812,930, filed Jul. 29, 2015, Weitz et al.
U.S. Appl. No. 14/812,942, filed Jul. 29, 2015, Weitz et al.
U.S. Appl. No. 14/812,951, filed Jul. 29, 2015, Weitz et al.
U.S. Appl. No. 14/812,946, filed Jul. 29, 2015, Weitz et al.
U.S. Appl. No. 14/812,954, filed Jul. 29, 2015, Weitz et al.
U.S. Appl. No. 14/812,964, dated Jul. 29, 2015, Weitz et al.
U.S. Appl. No. 15/528,905, filed May 23, 2017, Weitz et al.
U.S. Appl. No. 15/035,167, filed May 6, 2016, Weitz et al.
PCT/US2008/003185, Oct. 22, 2008, Invitation to Pay Additional Fees.
U.S. Appl. No. 15/768,135, filed Apr. 13, 2018, Weitz et al.
PCT/US2018/047053, Oct. 23, 2018, International Search Report and Written Opinion.
PCT/US2008/003185, Jan. 12, 2009, International Search Report and Written Opinion.
PCT/US2008/003185, Sep. 17, 2009, International Preliminary Report on Patentability.
PCT/US2008/008563, Oct. 29, 2008, International Search Report and Written Opinion.

(56) References Cited

OTHER PUBLICATIONS

CN 200880127116.4, Jun. 18, 2012, Chinese Office Action.
CN 200880127116.4, May 23, 2013, Chinese Office Action.
CN 200880127116.4, Dec. 24, 2013, Chinese Office Action.
EP 08865992.5, Dec. 15, 2010, European Office Communication.
EP 08865992.5, Jan. 23, 2012, European Office Communication.
EP 08865992.5, Apr. 5, 2013, European Office Communication.
EP 08865992.5, Aug. 29, 2013, European Office Communication.
EP 08865992.5, Apr. 29, 2014, European Office Communication.
JP 2010-539498, Jul. 17, 2013, Japanese Office Action.
JP 2010-539498, Sep. 2, 2014, Japanese Office Action.
PCT/US2008/013912, Apr. 3, 2009, International Search Report and Written Opinion.
PCT/US2008/013912, Jul. 1, 2010, International Preliminary Report on Patentability.
PCT/US2009/005184, May 27, 2010, Invitation to Pay Additional Fees.
PCT/US2009/005184, Aug. 16, 2010, International Search Report and Written Opinion.
PCT/US2009/005184, Mar. 31, 2011, International Preliminary Report on Patentability.
EP 09758762.0, Aug. 13, 2015, European Office Action.
EP 9758762.0, Sep. 29, 2016, European Office Action.
KR 10-2011-7000094, Feb. 27, 2013, Office Action.
PCT/US2009/003389, Oct. 21, 2009, International Search Report and Written Opinion.
PCT/US2009/003389, Dec. 16, 2010, International Preliminary Report on Patentability.
PCT/US2009/004037, Oct. 2, 2009, International Search Report and Written Opinion.
EP 9804166.8, Nov. 7, 2014, European Office Action.
PCT/US2009/006649, Mar. 10, 2010, International Search Report and Written Opinion.
PCT/US2009/006649, Jun. 30, 2011, International Preliminary Report on Patentability.
AU 2010315580, Dec. 17, 2013, Australian Office Action.
CN 201080055990.9, Dec. 16, 2013, Chinese Office Action.
CN 201080055990.9, Jul. 30, 2014, Chinese Office Action.
JP 2012-536941, Nov. 19, 2013, Japanese Office Action.
JP 2012-536941, Aug. 5, 2014, Japanese Office Action.
PCT/US2010/054050, Jan. 31, 2011, International Search Report and Written Opinion.
PCT/US2010/054050, May 10, 2012, International Preliminary Report on Patentability.
PCT/US2016/056509, Jan. 10, 2017, International Search Report and Written Opinion.
EP 14860623.9, May 23, 2017, Extended European Search Report.
PCT/US2014/063846, Jan. 7, 2015, Invitation to Pay Additional Fees and Partial Search Report.
PCT/US2014/063846, Mar. 10, 2015, International Search Report and Written Opinion.
PCT/US2014/063846, May 19, 2016, International Preliminary Report on Patentability.
International Search Report and Written Opinion for Application No. PCT/US2018/047053 dated Oct. 23, 2018.
Extended European Search Report for Application No. EP 16856059.7 dated Apr. 1, 2019.
Office Action for U.S. Appl. No. 13/119,470 dated Apr. 24, 2013.
Final Office Action for U.S. Appl. No. 13/119,470 dated Dec. 5, 2013.
Advisory Action for U.S. Appl. No. 13/119,470 dated Mar. 21, 2014.
Office Action dated Jun. 24, 2015 for U.S. Appl. No. 13/119,470.
Invitation to Pay Additional Fees for PCT/US2008/003185 dated Oct. 22, 2008.
International Search Report and Written Opinion of the International Searching Authority for International Application No. PCT/US2008/003185, dated Jan. 12, 2009.
International Preliminary Report on Patentability for PCT/US2008/003185 dated Sep. 17, 2009.
International Search Report and Written Opinion of the International Searching Authority for International Application No. PCT/US2008/008563, dated Oct. 29, 2008.
Chinese Office Action dated Jun. 18, 2012 for CN Application No. 200880127116.4.
Chinese Office Action dated May 23, 2013 for Application No. CN 200880127116.4.
Chinese Office Action dated Dec. 24, 2013 for CN Application No. 200880127116.4.
Office Communication dated Dec. 15, 2010 for Application No. EP 08865992.5.
Office Communication dated Jan. 23, 2012 for Application No. EP 08865992.5.
Office Communication dated Apr. 5, 2013 for Application No. EP 08865992.5.
Office Communication dated Aug. 29, 2013 for Application No. EP 08865992.5.
Office Communication dated Apr. 29, 2014 for EP Application No. EP 08865992.5.
Japanese Office Action dated Jul. 17, 2013 for Application No. JP 2010-539498.
Japanese Office Action dated Sep. 2, 2014 for Application No. JP 2010-539498.
International Search Report and Written Opinion of the International Searching Authority for International Application No. PCT/US2008/013912, dated Apr. 3, 2009.
International Preliminary Report on Patentability for PCT/US2008/013912 dated Jul. 1, 2010.
Invitation to Pay Additional Fees for PCT Application PCT/US09/005184 dated May 27, 2010.
International Search Report and Written Opinion from PCT Application PCT/US09/005184 dated Aug. 16, 2010.
International Preliminary Report on Patentability for PCT Application PCT/US09/005184 dated Mar. 31, 2011.
European Office Action for Application No. EP 09758762.0 dated Aug. 13, 2015.
European Office Action for Application No. 09758762.0 dated Sep. 29, 2016.
Korean Office Action for Application No. KR 10-2011-7000094 dated Feb. 27, 2013.
International Search Report and Written Opinion for International Application No. PCT/US09/003389 dated Oct. 21, 2009.
International Preliminary Report on Patentability for International Application No. PCT/US2009/003389 dated Dec. 16, 2010.
International Search Report and Written Opinion of the International Searching Authority for International Application No. PCT/US2009/004037, dated Oct. 2, 2009.
European Office action dated Nov. 7, 2014 for Application No. EP 09804166.8.
International Search Report and Written Opinion for International Application No. PCT/US2009/006649 dated Mar. 10, 2010.
International Preliminary Report on Patentability for International Application No. PCT/US2009/006649 dated Jun. 30, 2011.
Australian Office Action dated Dec. 17, 2013 for Application No. AU 2010315580.
Chinese Office Action dated Dec. 16, 2013 for Application No. CN 201080055990.9.
Chinese Office Action dated Jul. 30, 2014 for Application No. CN 201080055990.9.
Japanese Office Action dated Nov. 19, 2013 for Application No. JP 2012-536941.
Japanese Office Action dated Aug. 5, 2014 for Application No. JP 2012-536941.
International Search Report and Written Opinion from PCT Application PCT/US2010/054050 dated Jan. 31, 2011.
International Preliminary Report on Patentability from PCT Application PCT/US2010/054050 dated May 10, 2012.
International Search Report and Written Opinion dated Jan. 10, 2017 for Application No. PCT/US2016/056509.
Extended European Search Report for Application No. EP 14860623.9 dated May 23, 2017.
International Search Report and Written Opinion from PCT/US2014/063846 dated Mar. 10, 2015.

(56) References Cited

OTHER PUBLICATIONS

Invitation to Pay Additional Fees and Partial Search Report for Application No. PCT/US2014/063846 dated Jan. 7, 2015.
International Preliminary Report on Patentability from PCT Application PCT/US2014/063846 dated May 19, 2016.
Office Action for U.S. Appl. No. 13/119,470 dated Feb. 1, 2018.
Office Action for U.S. Appl. No. 14/812,930 dated Nov. 13, 2017.
Office Action for U.S. Appl. No. 14/812,942 dated Feb. 1, 2018.
Office Action for U.S. Appl. No. 14/812,951 dated Jan. 25, 2018.
Office Action for U.S. Appl. No. 14/812,946 dated Jan. 25, 2018.
Office Communication for U.S. Appl. No. 14/812,954 dated Dec. 7, 2017.
Office Action for U.S. Appl. No. 14/812,964 dated Jan. 25, 2018.
Office Action for U.S. Appl. No. 15/035,167 dated May 16, 2017.
Office Action for U.S. Appl. No. 15/035,167 dated Nov. 27, 2017.
[No Author Listed], Toxnet, Toxicology Data Network. Vinyl Toluene. National Library of Medicine. 2015:1-38.
[No Author] Gene Characterization Kits. Stratagene Catalog. Statagene Cloning Systems: Tools and Technology for Lift Sciences. 1988. 3 pages.
[No Author] Microfluidic ChipShop. Microfluidic product catalogue. Mar. 2005.
[No Author] Microfluidic ChipShop. Microfluidic product catalogue. Oct. 2009.
Abate et al., Droplet Based Sequencing. American Physical Society. Presentation. Mar. 12, 2008. 25 pages.
Abate et al., Valve-based flow focusing for drog formation. Appl Phys Lett. 2009;94. 3 pages. (Month not cited on publication).
Abate et al., High-throughput injection with microfluidics using picoinjectors. Proc Natl Acad Sci U S A. Nov. 9, 2010;107(45):19163-6. doi: 10.1073/pnas.1006888107. Epub Oct. 20, 2010.
Adams et al., Entropically driven microphase transitions in mixtures of colloidal rods and spheres. Nature. May 28, 1998:393:349-52.
Agresti, "Selection of ribozymes that catalyse multiple-turnover Diels-Alder cycloadditions by using in vitro compartmentalization", PNAS, 102, 16170-16175 (2005). (Nov. 2005).
Agresti et al., Ultrahigh-throughput screening in drop-based microfluidics for directed evolution. Proc Natl Acad Sci U S A. Mar. 2, 2010;107(9):4004-9. doi: 10.1073/pnas.0910781107. Epub Feb. 8, 2010. Erratum in: Proc Natl Acad Sci U S A. Apr. 6, 2010;107(14):6550.
Akselband, "Enrichment of slow-growing marine microorganisms from mixed cultures using gel microdrop (GMD) growth assay and fluorescence-activated cell sorting", J. Exp. Marine Biol., 329: 196-205 (2006). (Month not cited on publication).
Akselband, "Rapid mycobacteria drug susceptibility testing using gel microdrop (GMD) growth assay and flow cytometry", J. Microbiol. Methods, 62:181-197 (2005). (Month not cited on publication).
Anna et al., Formation of dispersions using 'flow focusing' in microchannels. Appln Phys Letts. 2003;82(3):364-66. (Jan. 2003).
Baret et al., Fluorescence-activated droplet sorting (FADS): efficient microfluidic cell sorting based on enzymatic activity. Lab Chip. Jul. 7, 2009;9(13):1850-8. doi: 10.1039/b902504a. Epub Apr. 23, 2009.
Boone, et al. Plastic advances microfluidic devices. The devices debuted in silicon and glass, but plastic fabrication may make them hugely successful in biotechnology application. Analytical Chemistry. Feb. 2002; 78A-86A.
Braeckmans et al., Scanning the Code. Modern Drug Discovery. 2003:28-32. (Feb. 2003).
Carroll, "The selection of high-producing cell lines using flow cytometry and cell sorting", Exp. Op. Biol. Therp., 4:11 1821-1829 (2004). (Month not cited on publication).
Chaudhary "A rapid method of cloning functional variable-region antibody genese in *Escherichia coli* as single-chain immunotoxins" Proc. Natl. Acad. Sci USA 87: 1066-1070 (Feb. 1990).
Chechetkin et al., Sequencing by hybridization with the generic 6-mer oligonucleotide microarray: an advanced scheme for data processing. J Biomol Struct Dyn. Aug. 2000;18(1):83-101. (Month not cited on publication).

Chou, et al. Disposable Microdevices for DNA Analysis and Cell Sorting. Proc. Solid-State Sensor and Actuator Workshop, Hilton Head, SC. Jun. 8-11, 1998; 11-14.
Chu, L., et al., "Controllable Monodisperse Multiple Emulsions," Angew. Chem. Int. Ed., vol. 46, pp. 8970-8974 (2007). (Month not cited on publication).
Clausell-Tormos et al., Droplet-based microfluidic platforms for the encapsulation and screening of Mammalian cells and multicellular organisms. Chem Biol. May 2008;15(5):427-37. doi: 10.1016/j.chembiol.2008.04.004. Erratum in: Chem Biol. Aug. 25, 2008;15(8):875.
De Bruin et al., UBS Investment Research. Q-Series® : DNA Sequencing. UBS Securities LLC. Jul. 12, 2007. 15 pages.
Dendukuri et al. Continuous-flow lithography for high-throughput microparticle synthesis. Nature Mat. May 2006;5:365-69.
Diaz, R.V., et al., "One-Month sustained release microspheres of 125 I-bovine calcitonin In Vitro-in vivo studies," Journal of Controlled Release, vol. 59, pp. 55-62 (1999). (Month not cited on publication).
Doerr, The smallest bioreactor. Nature Methods. 2005; 2(5):326. (May 2005).
Draget et al., Alginate based new materials. Int J Biol Macromol. Aug. 1997;21(1-2):47-55.
Drmanac eta l., Sequencing by hybridization (SBH): advantages, achievements, and opportunities. Adv Biochem Eng Biotechnol. 2002;77:75-101. (Month not cited on publication).
Durant et al., Effects of cross-linking on the morphology of structured latex particles 1. Theoretical considerations. Macromol. 1996;29:8466-72. Month not cited on publication.
Fu, "A microfabricated fluorescence-activated cell sorter", Nature Biotech., 17:1109-1111 (1999). (Nov. 1999).
Fulton et al., Advanced multiplexed analysis with the FlowMetrix system. Clin Chem. Sep. 1997;43(9):1749-56.
Gartner, et al. The Microfluidic Toolbox—examples for fluidic interfaces and standardization concepts. Proc. SPIE 4982, Microfluidics, BioMEMS, and Medical Microsystems, (Jan. 17, 2003); doi: 10.1117/12.479566.
Ghadessy et al. Directed evolution of polymerase function by compartmentalized self-replication. Proc Natl Acad Sci USA. Apr. 10, 2001; 98(8):4552-7. Epub Mar. 27, 2001.
Gordon et al., Self-assembled polymer membrane capsules inflated by osmotic pressure. JACS. 2004;126:14117-22. Published on web Oct. 12, 2004.
Graham et al., Nanogels and microgels: The new polymeric materials playground. Pure Appl Chem. 1998;70(6):1271-75. Month not cited on publication.
Guo et al., Droplet microfluidics for high-throughput biological assays. Lab Chip. Jun. 21, 2012;12(12):2146-55. doi: 10.1039/c2lc21147e. Epub Feb. 9, 2012.
He et al., "Selective Encapsulation of Single Cells and Subcellular Organelles into Picoliter—and Femtoliter—Volume Droplets" Anal. Chem 77: 1539-1544 (2005) (Mar. 2005).
Holtze et al., Biocompatible surfactants for water-in-fluorocarbon emulsions. Lab Chip. Oct. 2008; 8(10):1632-9.
Hsu et al., Self-assembled shells composed of colloidal particles: fabrication and characterization. Langmuir. 2005;21:2963-70. Published on web Feb. 23, 2005.
Huebner, "Quantitative detection of protein expression in single cells using droplet microfluidics", Chem. Commun. 1218-1220 (2007). (Month not cited on publication).
Hug et al. Measurement of the number of molecules of a single mRNA species in a complex mRNA preparation. J Theor Biol. Apr. 21, 2003; 221(4):615-24.
Jogun et al., Rheology and microstructure of dense suspensions of plate-shaped colloidal particles. J. Rheol. Jul./Aug. 1999;43:847-71.
Khatiwala et al., "Intrinsic mechanical properties of the extracellular matrix affect the behaviour of pre-osteoblastic MC3T3-E1 cells" Am. J. Physiol. Cell Physiol. 2006;290:C1640.
Khetani et al., Microscale culture of human liver cells for drug development. Nat Biotechnol. Jan. 2008;26(1):120-6. Epub Nov. 18, 2007.

(56) References Cited

OTHER PUBLICATIONS

Khomiakova et al., [Analysis of perfect and mismatched DNA duplexes by a generic hexanucleotide microchip]. Mol Biol (Mosk). Jul.-Aug. 2003;37(4):726-41. Russian.
Kim et al., Colloidal assembly route for responsive colloidsomes with tunable permeability. Nano Lett. 2007;7:2876-80. Published on web Aug. 3, 2007.
Kim et al., Fabrication of monodisperse gel shells and functional microgels in microfluidic devices. Angew Chem Int Ed Engl. Mar. 2007;46(11):1819-22.
Kim et al., Monodisperse nonspherical colloid materials with well-defined structures. Presentation. Sep. 16, 2005. 5 pages.
Kim et al., Synthesis of nonspherical colloidal particles with anisotropic properties. JACS. 2006;128:14374-77. Published on web Oct. 18, 2006.
Kim et al., Uniform nonspherical colloidal particles engineered by geometrically tunable gradient of crosslink density. $80^{th}$ ACS Colloid Surf. Sci. Symp. Jun. 20, 2006. 23 pages.
Kim et al., Uniform nonspherical colloidal particles with tunable shapes. Adv. Mater. 2007;19:2005-09. Month not cited on publication.
Kim, "Fabrication of monodisperse gel shells and functional microgels in microfluidic devices", Angew. Chem., 119:1851-1854 (2007).
Kim, J., et al, "Albumin loaded microsphere of amphiphilic poly(ethylene glycol)/poly(a-ester) multiblock copolymer," European Journal of Pharmaceutical Sciences, vol. 23, pp. 245-251 (2004). (Month not cited on publication).
Klein et al., Cell-cycle control by physiological matrix elasticity and in vivo tissue stiffening. Curr Biol. Sep. 29, 2009;19(18):1511-8. doi: 10.1016/j.cub.2009.07.069. Epub Sep. 17, 2009.
Koo et al., A snowman-like array of colloidal dimers for antireflecting surfaces. Adv Mater. Feb. 3, 2004;16(3):274-77.
Koster et al., "Drop-based microfluidic devices for encapsulation of single cells", Lab on a Chip the Royal Soc. of Chem. 8:1110-1115 (2008). (Month not cited on publication).
Kumar et al., Biodegradable block copolymers. Adv Drug Deliv Rev. Dec. 3, 2001;53(1):23-44.
Kumaresan et al. High-Throughput Single Copy DNA Amplification and Cell Analysis in Engineered Nanoliter Droplets. Anal Chem. 2008. 80:3522-3529.
Landfester et al. Preparation of Polymer Particles in Nonaqueous Direct and Inverse Miniemulsions. Macromolecules. Mar. 11, 2000;33(7):2370-2376.
Landfester et al., Formulation and Stability Mechanisms of Polymerizable Miniemulsions. Macromolecules. 1999;32:5222-5228. Published on web Jul. 22, 1999.
Lee et al., Double emulsion-templated nanoparticle colloidosomes with selective permeability. Adv Mater. 2008;20:3498-503. Month not cited on publication.
Lee et al., Alginate: properties and biomedical applications. Prog Polym Sci. Jan. 2012;37(1):106-126.
Li, Y., et al., "PEGylated PLGA nanoparticles as protein carriers: synthesis, preparation and biodistribution in rats," Journal of Controlled Release, vol. 71, pp. 203-211 (2001). (Month not cited on publication).
Lin et al., Ultrathin cross-linked nanoparticle membranes. JACS. 2003;125:12690-91. Published on web Sep. 27, 2003.
Lorenceau et al., Generation of polymerosomes from double-emulsions. Langmuir. Sep. 27, 2005;21(20):9183-6.
Loscertales, Micro/Nano encapsulation via electrified coaxial liquid jets. Science. 2002;295:1695-98. (Mar. 2002).
Love, A microengraving method for rapid selection of single cells producing antigen-specific antibodies. Nature Biotech. Jun. 2006:24(6):703-07.
Manoharan et al., Dense packing and symmetry in small clusters of microspheres. Science. Jul. 25, 2003;301:483-87.
Mazutis et al., Selective droplet coalescence using microfluidic systems. Lab Chip. Apr. 24, 2012; 12(10):1800-6.

Mirzabekov, "DNA Sequencing by Hybridization—a Megasequencing Method and a Diagnostic Tool?" Trends in Biotechnology 12(1): 27-32 (1994) (Jan. 1994).
Mock et al., Synthesis of anisotropic nanoparticles by seeded emulsion polymerization. Langmuir. Apr. 25, 2006;22(9):4037-43. Published on web Mar. 31, 2006.
Mouritzen et al., Single nucleotide polymorphism genotyping using locked nucleic acid (LNA). Expert Rev Mol Diagn. Jan. 2003;3(1):27-38.
Nguyen, "In situ hybridization to chromosomes stabilized in gel microdrops", Cytometry, 21:111-119 (1995). (Month not cited on publication).
Nikolaides et al., Two Dimensional Crystallisation on Curved Surfaces. MRS Fall 2000 Meeting. Boston, MA. Nov. 27, 2000. Abstract #41061.
Okubo et al., Micron-sized, monodisperse, snowman/confetti-shaped polymer particles by seeded dispersion polymerization. Colloid Polym. Sci. 2005;283:1041-45. Published online Apr. 2, 2005.
Okushima, "Controlled production of monodisperse double emulsions by two-step droplet breakup in microfluidic devices", Langmuir, 20:9905-9908 (2004). (Month not cited on publication).
Park et al., Shear-reversibly crosslinked alginate hydrogels for tissue engineering. Macromol Biosci. Sep. 9, 2009;9(9):895-901. doi: 10.1002/mabi.200800376.
Perez, C., et al., "Poly(lactic acid)-poly(ethylene glycol) nanoparticles as new carriers for the delivery of plasmid DNA," Journal of Controlled Release, vol. 75, pp. 211-224 (2001). (Month not cited on publication).
Reculusa et al., Synthesis of daisy-shaped and multipod-like silica/polystyrene nanocomposites. Nano Lett. 2004;4:1677-82. Published on web Jul. 14, 2004.
Rimann et al., Synthetic 3D multicellular systems for drug development. Curr Opin Biotechnol. Oct. 2012;23(5):803-9. doi:10.1016/j.copbio.2012.01.011. Epub Feb. 10, 2012.
Roh et al., Biphasic janus particles with nanoscale anisotropy. Nature Med. Oct. 2005;4:759-63.
Ryan, "Rapid assay for mycobacterial growth and antibiotic susceptibility using gel microdrop and encapsulation", J. Clinical Microbiol., 33:7 1720-1726 (1995). (Jul. 1995).
Sakai et al., Both ionically and enzymatically crosslinkable alginate-tyramine conjugate as materials for cell encapsulation. J Biomed Mater Res A. May 2008;85(2):345-51.
Schirinzi et al., Combinatorial sequencing-by-hybridization: analysis of the NF1 gene. Genet Test. 2006 Spring;10(1):8-17. (Month not cited on publication).
Schmitt, "Bead-based multiplex genotyping of human papillomaviruses", J. Clinical Microbiol., 44:2 504-512 (2006). (Feb. 2006).
Schmitz et al., Dropspots: a picoliter array in a microfluidic device. Lab Chip. Jan. 7, 2009;9(1):44-9. doi: 10.1039/b809670h. Epub Oct. 28, 2008.
Schürch et al., "Potential of plant cells in culture for cosmetic applications." Phytochem. Rev. 2008;7:599.
Shah, "Fabrication of monodisperse thermosensitive microgels and gel capsules in microfluidic devices", Soft Matter, 4:2303-2309 (2008). (Month not cited on publication).
Sheu et al., Phase separation in polystyrene latex interpenetrating polymer networks. J. Poly. Sci. A. Poly. Chem. 1990;28:629-51. Month not cited on publication.
Shintaku et al. Micro cell encapsulation and its hydrogel-beads production using microfluidic device. Microsyst Technol. 2007. 13:951-958.
Shum et al., Double emulsion templated monodisperse phospholipid vesicles. Langmuir. Aug. 5, 2008;24(15):7651-3. Epub Jul. 10, 2008.
Shum et al., Microfluidic fabrication of monodisperse biocompatible and biodegradable polymersomes with controlled permeability. J Am Chem Soc. Jul. 23, 2008;130(29):9543-9. Epub Jun. 25, 2008.
Simeonov et al., Single nucleotide polymorphism genotyping using short, fluorescently labeled locked nucleic acid (LNA) probes and fluorescence polarization detection. Nucleic Acids Res. Sep. 1, 2002;30(17):e91.

(56) References Cited

OTHER PUBLICATIONS

Skjeltorp et al., Preparation of nonspherical, monodisperse polymer particles and their self-organization. J. Colloid Interf. Sci. Oct. 1986;113:577-82.

Sorokin et al., Discrimination between perfect and mismatched duplexes with oligonucleotide gel microchips: role of thermodynamic and kinetic effects during hybridization. J Biomol Struct Dyn. Jun. 2005;22(6):725-34.

Su et al., Microfluidics-Based Biochips: Technology Issues, Implementation Platforms, and Design-Automation Challenges. IEEE Transactions on Computer-Aided Design of Integrated Circuits and Systems. 2006;25(2):211-23. (Feb. 2006).

Sun et al., Progress in research and application of liquid-phase chip technology. Chinese Journal Experimental Surgery. May 2005;22(5):639-40.

Tan et al., "Monodisperse Alginate Hydrogel Microbeads for Cell Encapsulation" Adv. Mater. 2007;19:2696.

Tawfik, et al. Man-made cell-like compartments for molecular evolution. Nat Biotechnol. Jul. 1998;16(7):652-6.

Ulrich, Chapter 1. General Introduction. Chem. Tech. Carbodiimides. 2007:1-7. Month not cited on publication.

Van Blaaderen, Colloidal molecules and beyond. Science. Jul. 25, 2003;301:470-71.

Van Blaaderen, Colloids get complex. Nature. Feb. 2006;439:545-46.

Van De Hulst et al., Glare points. Appl Opt. Nov. 20, 1991;30(33):4755-63.

Velasco., Microfluidic encapsulation of cells in polymer microgels. Small. Jun. 11, 2012;8(11):1633-42. doi: 10.1002/smll.201102464. Epub Mar. 29, 2012.

Velev et al., Assembly of latex particles by using emulsion droplets. 3. Reverse (water in oil) system. Langmuir. 1997;13:1856-59. Month not cited on publication.

Velev et al., Assembly of latex particles using emulsion droplets as templates. 1. Microstructured hollow spheres. Langmuir. 1996;12:2374-84. Month not cited on publication.

Velev et al., Assembly of latex particles using emulsion droplets as templates. 2. Ball-like and composite aggregates. Langmuir. 1996;12:2385-91. Month not cited on publication.

Wang et al., Single nucleotide polymorphism discrimination assisted by improved base stacking hybridization using oligonucleotide microarrays. Biotechniques. 2003;35:300-08. (Aug. 2003).

Weaver, "Rapid clonal growth measurements at the single-cell level: gel microdroplets and flow cytometry", Biotechnology, 9:873-877 (1991). (Sep. 1991).

Weitz, Nonspherical engineering of polymer colloids. Web Page. Exp. Soft Condensed Matter Group. Last updated Nov. 10, 2005. 1 page.

Weitz, Packing in the spheres. Science. Feb. 13, 2004;303:968-969.

Whitesides, "Soft lithography in biology and biochemistry", Annual Review of Biomedical Engineering, 3:335-373 (2001). (Month not cited on publication).

Xia, "Soft lithography", Annual Review of Material Science, 28:153-184 (1998). (Month not cited on publication).

Yin et al., Template-assisted self-assembly: a practical route to complex aggregates of monodispersed colloids with well-defined sizes, shapes, and structures. JACS. 2001;123:8718-29. Published on web Aug. 15, 2001.

Zhang, "Combinatorial marking of cells and organelles with reconstituted fluorescent proteins", Cell, 119:137-144 (Oct. 1, 2004).

Zhang et al., "Microfluidic Production of Biopolymer Microcapsules with Controlled Morphology." JACS. 2006;128:12205.

Zhang et al., "Exploring Microfluidic Routes to Microgels of Biological Polymers." Macromol. Rapid. Commun. vol. 280, Issue 5, p. 327 (2007).

Zhao, J., et al., "Preparation of hemoglobin-loaded nano-sized particles with porous structure as oxygen carriers," Biomaterials, vol. 28, pp. 1414-1422 (2007). Available online Nov. 2006.

Zimmerman, Microscale production of hybridomas by hypoosmolar electrofusion. Hum Antibod Hybridomas. 1992;3 Jan. 14-18.

\* cited by examiner a)

b)

a)

b)

c)

MICROPARTICLES, METHODS FOR THEIR PREPARATION AND USE

CLAIM OF PRIORITY

This application is a divisional of U.S. patent application Ser. No. 15/035,167, filed May 6, 2016, which is a U.S. national stage filing under 35 U.S.C. 371 of International Patent Application Serial No. PCT/US2014/063846, filed Nov. 4, 2014, which claims priority to U.S. Provisional Patent Application Ser. No. 61/901,949, filed Nov. 8, 2013, each of which is hereby incorporated by reference in its entirety.

GOVERNMENT FUNDING

This invention was made with government support under Grant No. EB014703 awarded by National Institutes of Health, and under Grant Nos. 1310266 and 0820484 awarded by National Science Foundation. The government has certain rights in the invention.

BACKGROUND OF THE INVENTION

Microparticles formed from a crosslinked gel hold great potential for applications involving the encapsulation and release of actives for application in agriculture, encapsulation of food ingredients, health care, cosmetics, tissue engineering, sensors, optical components, coatings (e.g., paints and pigments), additives, catalysis, and oil recovery. Despite their potential, it is very difficult to obtain (hydro)gel microparticles having a defined shape and at least one dimension that is in the order of 50 µm or less. In addition, it is difficult to control the distribution of the crosslinking agent used to form the gel that makes up the microparticle and to guarantee for a reliable, reproducible, and structural homogenous gelation.

SUMMARY OF THE INVENTION

Embodiments of the present invention are directed to microparticles and methods for making such microparticles. Such microparticles are characterized by a high degree of monodispersity and structural homogeneity. The methods for forming such microparticles described herein demonstrate a high degree of flexibility regarding size, shape, and morphology of the resulting microparticles. For example, microfluidic techniques can be used to prepare rods, crescents, hooks, as well as core-shell microparticles. Additionally, cells, including multiple (e.g., biofilms), as well as single cells, can be encapsulated in the microparticles, which allows for long-term cell culture of individual cells in an independent microenvironment. Further, there is an ability to grow identical colonies (i.e., clones) of cells (e.g., bacteria) using the microparticles of the embodiments of the present invention to encapsulate such cells.

The microparticles of the embodiments of the present invention can be used in a number of technological areas, including in the areas of pharmaceuticals, biotechnology, cosmetics, food additives, optical devices (e.g., lenses) and sensors.

The ability to generate three dimensional cell systems has an enormous potential to increase the biological accuracy and physiological relevance of cell-based efficacy and toxicological tests in the pharmaceutical industry. Three-dimensional cell culture techniques not only offer excellent extracellular matrix and tissue mimics, but also allow for high-throughput analysis and applications, especially in micron-sized systems. Hence, time and costs of relevant screening processes can be drastically reduced, resulting in a more efficient drug developing process. See, e.g., Rimann et al. *Curr. Opin. Biotechnol.* 23: 803 (2012).

The microparticles of the embodiments of the present invention can be used in drug delivery and drug release applications. By controlling the size, shape, and morphology, as well as the mechanical properties of the microparticles, release profiles and in vivo applicability can be improved and controlled.

Another area of possible applications for the microparticles of the embodiments of the present invention is regenerative medicine and tissue engineering. Microparticles comprising cells can act as scaffolds or modules for transplants. Alginate, for example, has shown great potential in enhancing the regeneration and formation of bones, cartilage, skeletal muscles, nerves, pancreas, and blood vessels. Lee et al. *Prog. Polym. Sci.* 37: 106 (2012). Their small size makes the presented cell-containing microparticles excellent candidates for injectable delivery vehicles in tissue engineering allowing for a tissue formation in a minimal invasive method. Park et al. *Macromol. Biosci.* 9: 895 (2009).

In the area of cosmetics, the microparticles of certain embodiments of the present invention may be used, for example, to deliver stem cells in products designed to lift, protect or enhance the skin. See, e.g., Cosmetic and Pharmaceutical Applications of Polymers (Gebelein et al. eds. Plenum 1991); and Schüarch et al. *Phytochem. Rev.* 7: 599 (2008).

The microparticles of the embodiments of the present invention can also be used in the construction of lenses or sensor systems. By virtue of their mechanical, chemical, and morphological properties, in conjunction with the natural response to environmental conditions, renders the microparticles of the embodiments of the present invention useful in optical devices and sensors. Microgel Suspensions (Fernandez-Nieves eds., Wiley 2011).

In various embodiments, the invention relates to microparticles comprising: a crosslinked gel; wherein the microparticles have a coefficient of variation in the size distribution of the microparticles of from about 0.03 to about 0.05 and wherein the microparticles have at least one dimension measuring from about 5 nm to about 200 nm.

In various other embodiments, the invention relates to microparticles comprising: a $Ca^{2+}$-crosslinked alginate gel; wherein the microparticles have a coefficient of variation in the size distribution of the microparticles of from about 0.03 to about 0.05 and wherein the microparticles have at least one dimension measuring from about 5 nm to about 200 µm.

In still other embodiments, the invention relates to a method of forming the microparticles, the method comprising: forming microdroplets comprising one or more crosslinkable linear polysaccharides and one or more crosslinking agents; contacting the microdroplets with a crosslinking promoter to promote crosslinking of the one or more crosslinkable linear polysaccharides.

In yet other embodiments, the invention relates to a method of forming the microparticles, the method comprising: forming microdroplets comprising alginate and $Ca^{2+}$-EDTA; and contacting the microdroplets with a crosslinking promoter to promote crosslinking of the alginate.

BRIEF DESCRIPTION OF THE FIGURES

The drawings illustrate generally, by way of example, but not by way of limitation, various embodiments discussed in the present document.

DETAILED DESCRIPTION OF THE INVENTION

Figure 1:
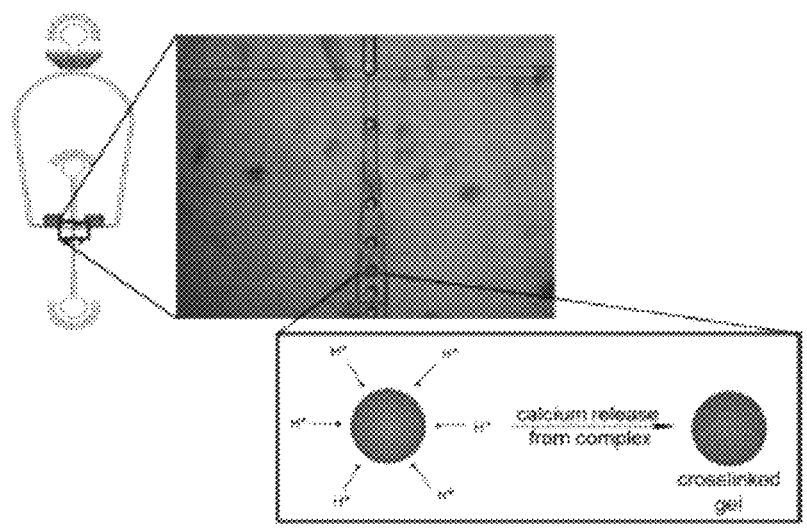
FIG. 1 is a scheme showing the formation of alginate microparticles using a 50 μm polydimethylsiloxane (PDMS) dropmaker (panel a)) and microscopic images of resulting alginate microparticles in the size range of 15-50 μm after transfer into aqueous medium (panel b)).
Figure 1:

Reference will now be made in detail to certain embodiments of the disclosed subject matter, examples of which are illustrated in part in the accompanying drawings. While the disclosed subject matter will be described in conjunction with the enumerated claims, it will be understood that the exemplified subject matter is not intended to limit the claims to the disclosed subject matter.

Values expressed in a range format should be interpreted in a flexible manner to include not only the numerical values explicitly recited as the limits of the range, but also to include all the individual numerical values or sub-ranges encompassed within that range as if each numerical value and sub-range were explicitly recited. For example, a range of "about 0.1% to about 5%" or "about 0.1% to 5%" should be interpreted to include not just about 0.1% to about 5%, but also the individual values (e.g., 1%, 2%, 3%, and 4%) and the sub-ranges (e.g., 0.1% to 0.5%, 1.1% to 2.2%, 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

In this document, the terms "a," "an," or "the" are used to include one or more than one unless the context clearly dictates otherwise. The term "or" is used to refer to a nonexclusive "or" unless otherwise indicated. In addition, it is to be understood that the phraseology or terminology employed herein, and not otherwise defined, is for the purpose of description only and not of limitation. Any use of section headings is intended to aid reading of the document and is not to be interpreted as limiting; information that is relevant to a section heading may occur within or outside of that particular section. Furthermore, all publications, patents, and patent documents referred to in this document are incorporated by reference herein in their entirety, as though individually incorporated by reference. In the event of inconsistent usages between this document and those documents so incorporated by reference, the usage in the incorporated reference should be considered supplementary to that of this document; for irreconcilable inconsistencies, the usage in this document controls.

In the methods described herein, the steps can be carried out in any order without departing from the principles of the invention, except when a temporal or operational sequence is explicitly recited. Furthermore, specified steps can be carried out concurrently unless explicit claim language recites that they be carried out separately. For example, a claimed step of doing X and a claimed step of doing Y can be conducted simultaneously within a single operation, and the resulting process will fall within the literal scope of the claimed process.

The term "about" as used herein can allow for a degree of variability in a value or range, for example, within 10%, within 5%, or within 1% of a stated value or of a stated limit of a range.

The term "substantially" as used herein refers to a majority of, or mostly, as in at least about 50%, 60%, 70%, 80%, 90%, 95%, 96%, 97%, 98%, 99%, 99.5%, 99.9%, 99.99%, or at least about 99.999% or more.

Embodiments of the present invention relate to microparticles comprising a crosslinked gel, wherein the microparticles have at least one dimension measuring from about 1 μm to about 200 μm (e.g., from about 5 μm to about 200 μm; or from about 40 μm to about 200 μm). In some embodiments, the microparticles have a coefficient of variation of from about 0.03 to about 0.05 (e.g., from about 0.04 to about 0.05, or from about 0.03 to about 0.04). The term "coefficient of variation" refers to the standard deviation of the size distribution of the microparticles, assuming a Gaussian distribution, divided by the mean size. The coefficient of variation is a measure of the size polydispersity observed for the contemplated microparticles. For non-spherical microparticles, the coefficient of variation is determined for each dimension of the particles, individually.

The microparticles may have any suitable dimensions and are, in some embodiments, substantially spherical such that the microparticles are substantially microspheres. But the microparticles may also be non-spherical and of any suitable shape, including oblong, rod-, crescent- or hook-shaped. The microparticles can also be core-shell microparticles where the microparticles may have a liquid core and a solid shell; a gas core and a solid shell; or a solid core and a solid shell, all of which may referred to as core-shell microparticles.

In some embodiments, the microparticles of the embodiments of the present invention may have at least one dimension measuring less than 200 μm, less than 150 μm, less than 100 μm, less than 75 μm, less than 65 μm, less than 55 μm, less than 45 μm or less than 35 μm, with a lower bound of about 1 μm; from about 5 μm to about 15 μm; from about 10 μm to about 200 μm, from about 10 μm to about 100 μm, from about 10 μm to about 75 μm, from about 30 μm to about 75 μm, from about 30 μm to about 100 μm or from about 50 μm to about 100 μm. In some embodiments, the microparticles of the embodiments of the present invention are substantially spherical and have a diameter less than 200 µm, less than 150 µm, less than 100 µm, less than 75 µm, less than 65 µm, less than 55 µm, less than 45 µm or less than 35 µm, with a lower bound of about 10 µm; from about 10 µm to about 200 µm, from about 10 µm to about 100 µm, from about 10 µm to about 75 µm, from about 30 µm to about 75 µm, from about 30 µm to about 100 µm, from about 50 µm to about 100 µm or from about 40 µm to about 200 µm.

When the microparticles of the embodiments of the present invention are core-shell microparticles, the shell may have any suitable thickness. In some embodiments, the shell has a thickness of from about 200 nm to about 200 µm, about 200 nm to about 750 nm, from about 200 nm to about 1 µm, from about 750 nm to about 50 µm, from about 1 µm to about 50 µm, from about 25 µm to about 50 µm, from about 2 µm to about 10 µm or from about 2 µm to about 5 µm. In some embodiments, the thickness of the shell can be substantially uniform or it can be non-uniform. It should be appreciated that when the shell reaches a thickness that equals the diameter of the microparticle, then the microparticle will no longer be a core-shell microparticle and will instead be a microparticle.

In some embodiments, the microparticles of the embodiments of the present invention can comprise nanoparticles. In some embodiments, the nanoparticles can be homogenously or inhomogeneously distributed throughout the microparticles. And in embodiments where the microparticles are core-shell microparticles, the nanoparticles can be homogeneously or inhomogeneously distributed throughout the core, the shell or both. In some embodiments, the nanoparticles can be magnetic nanoparticles (e.g., iron oxide nanoparticles).

In some embodiments, the microparticles of the embodiments of the present invention can be core-shell microparticles and comprise a solid or a liquid core (e.g., a substantially aqueous core comprising a substantially aqueous liquid). The solid core may be made of the same material as the shell or of a different material than the shell. In some embodiments, the core is a liquid core. In some embodiments, the liquid core may be an aqueous core. When the liquid core is an aqueous core, it may be a water-only aqueous core or the water may comprise one or more materials dissolved in the water including salts (e.g., NaCl and $MgCl_2$), buffers (e.g., phosphate buffer), acids (e.g., acetic acid and lactic acid), bases, cell growth medium, polymers (e.g., poly(ethylene glycol), dextran), nutrients, encapsulants, polymers, nanoparticles or combinations thereof.

In some embodiments, the liquid core may be a non-aqueous core that can comprise, e.g., an organic material including a solvent, a polymer, a dye, and the like.

In some embodiments, the core can be a solid core, a liquid core or a combination thereof. For example, the microparticles of the embodiments of the present invention may comprise a substantially solid core with liquid "pockets" distributed throughout the substantially solid core. The "pockets" may be of a uniform size or the size of the "pockets" may be variable.

In other embodiments, the core can be a solid core, a liquid core or a combination thereof, wherein the core can comprise nanoparticles (e.g., particles having at least one dimension having an average dimension of about 20 to about 500 nm, about 100 to about 500 nm, about 100 to about 300 nm or about 100 to about 200 nm) such as, but not limited to, magnetic nanoparticles such as iron oxide nanoparticles.

In some embodiments, microparticles comprising such nanoparticles in their core can be useful in magnetic field-induced self-assembly of macrometer-sized constructs as engineered tissues for regenerative medicine. In other embodiments, microparticles comprising such nanoparticles in their core can be useful as targeting delivery vehicles, such that a magnet or magnetic field placed at or near a target site (e.g., organ or other tissue) would guide the microparticles comprising such nanoparticles to and concentrated at or near a target site at or near the magnet or magnetic field. Among other things, anti-cancer drugs covalently or non-covalently attached to such nanoparticles could be delivered at or near a target site.

Microparticles containing nanoparticles smaller than 20 nm (e.g., 1-20 nm) are also contemplated herein. Such nanoparticles (e.g., functionalized magnetic nanoparticles such as are known in the art) can be encapsulated or cross-linked within the crosslinked gel, crosslinked with the gel or combinations thereof.

In some embodiments, the aqueous or solid core and/or the shell can comprise viruses, one or more cells (e.g., mammalian cells, plant cells, bacteria, and combinations thereof) or proteins (e.g., collagen and antibodies). The cells or proteins can be substantially within the microparticles; may protrude into the exterior of the microparticles (e.g., through the shell of a core-shell microparticle); may protrude into the interior of the microparticles (e.g., through the shell of a core-shell microparticle and into the core); may protrude into the interior and the exterior of the microparticles (e.g., traversing the shell of a core-shell microparticle). In some embodiments, the core comprises a single cell or protein.

The encapsulation of cells in microparticles of the embodiments of the present invention may be advantageous for, e.g., long-term (e.g., twelve or more hours; fifteen or more hours; one or more days; five days to one month or more) cell culture of individual or multiple cells in an independent microenvironment. In addition, cells such as adherent cells can be cultured encapsulated in the microparticles of the embodiments of the present invention because the microparticles of certain embodiments of the present invention provide a solid support that allows for a natural adherence and spreading of the cells within the microparticle. The microparticles can then be transferred to a cell culture medium or media where the cells within the microparticles are guaranteed a sufficient nutrient supply, given the solidified spheres can, in some embodiments, be permeable to nutrients.

One advantage of having one or more cells or proteins protrude into the exterior of the microparticles, whether through the shell of a core-shell microparticle or a solid microparticle, is that the microparticle may have the propensity to form tissue-like assemblies. Briefly, by incorporating different cell types in in defined regions of the core-shell particles (e.g., encapsulation of one cell type into the core while a different cell type is incorporated into the shell of the particle) the balance of homotypic and heterotypic interactions can be controlled. See, e.g., Khetani et al. *Nature Biotechnology* 26: 120-126 (2008).

In some embodiments, whether the core is a liquid core or a solid core, or combinations thereof, the core can comprise an active agent distributed in the core. In some embodiments, the active agent is a cell (e.g., a plant stem cell), a pharmaceutical agent, an agrochemical agent or a food additive. See, e.g., Rimann et al. *Curr. Opin. Biotechnol.* 23: 803 (2012); Lee et al. *Prog. Polym. Sci.* 37: 106 (2012); and Microgel Suspensions (Fernandez-Nieves eds., Wiley 2011).

Examples of pharmaceuticals include, but are not limited to, antibiotics, antitussives, antihistamines, decongestants, alkaloids, mineral supplements, laxatives, antacids, anticholesterolemics, antiarrhythmics, antipyretics, analgesics, appetite suppressants, expectorants, anti-anxiety agents, anti-ulcer agents, anti-inflammatory substances, coronary dilators, cerebral dilators, peripheral vasodilators, anti-infectives, psychotropics, antimanics, stimulants, gastrointestinal agents, sedatives, anti-diarrheal preparations, anti-anginal drugs, vasodialators, anti-hypertensive drugs, vasoconstrictors, migraine treatments, antibiotics, tranquilizers, anti-psychotics, antitumor drugs, anticoagulants, anti-thrombotic drugs, hypontics, anti-emetics, anti-nausants, anti-convulsants, neuromuscular drugs, hyper- and hypoglycemic spasmodics, uterine relaxants, mineral and nutritional additives, antiobesity drugs, anabolic drugs, erythropoetic drugs, antiashmatics, cough suppressants, mucolytics, anti-uricemic drugs, mixtures thereof, and the like. Examples of agrochemicals include, but are not limited to, chemical pesticides (such as herbicides, algicides, fungicides, bactericides, viricides, insecticides, acaricides, miticides, nematicides, and molluscicides), herbicide safeners, plant growth regulators, fertilizers and nutrients, gametocides, defoliants, desiccants, mixtures thereof and the like. Examples of food additives include, but are not limited to, caffeine, taste-masking agents, vitamins, minerals, color additives, herbal additives (e.g., echinacea or St. John's Wort), antimicrobials, preservatives, mixtures thereof, and the like.

In some embodiments, the microparticles of the embodiments of the present invention may have pores. In some embodiments, the pores are distributed throughout the shell of core-shell microparticles of the embodiments of the present invention. The pores may have any suitable diameter and length. The pores may have, e.g., a diameter ranging from about 1 nm to about 5 µm, e.g., from about 5 nm to about 5 µm, from about 5 nm to about 750 nm, from about 50 nm to about 500 nm or from about 50 nm to about 250 nm, from about 50 nm to about 250 nm or from about 5 nm to about 1 µm. The diameter of the pores may or may not be uniform within a single pore or across a multitude of pores.

One of the functions of the pores is to serve as a conduit for any active agent to diffuse from the microparticle (e.g., from the core; through the shell) into the environment surrounding the microparticles of the embodiments of the present invention. Those of skill in the art will recognize, however, that the pores can also function as a conduit for materials located in the environment surrounding the microparticles of the embodiments of the present invention to diffuse into the microparticles. For example, in applications where one or more cells are located in the microparticles of the embodiments of the present invention, pores may play a key role as conduits for nutrients that are necessary for cell growth within the microparticles.

In some embodiments, the microparticles of the embodiments of the present invention are degradable (e.g., biodegradable). For example, the microparticles may be digestible by one or more enzymes or may degrade by hydrolysis. In other embodiments, the microparticles of the embodiments of the present invention are non-degradable or partially degradable.

Microparticles of the embodiments of the present invention may be made of any suitable cross-linkable material that can be subsequently cross-linked via any suitable means for cross-linking, thereby yielding a cross-linked gel. Examples of suitable cross-linkable materials include, but are not limited to, cross-linkable linear polysaccharides. In some embodiments, the cross-linkable material comprises homopolymeric blocks of (1-4)-linked β-D-mannuronate and α-L-guluronate. Non-limiting examples of cross-linkable materials that can be used to form the microparticles of the embodiments of the present invention include alginate, chitosan, curdlan, dextran, emulsan, a galactoglucopolysaccharide, gellan, glucuronan, N-acetyl-heparosan, hyaluronic acid, indicant, kefiran, lentinan, levan, mauran, pullulan, scleroglucan, schizophyllan, stewartan, succinoglycan, xanthan, xylane, welan, starch, tamarind, tragacanth, guar gum, derivatized guar, gum ghatti, gum arabic, locust bean gum, cellulose, hemicellulose, carboxymethyl cellulose, hydroxyethyl cellulose, carboxymethyl hydroxyethyl cellulose, hydroxypropyl cellulose, methyl hydroxyl ethyl cellulose, guar, hydroxypropyl guar, carboxy methyl guar, carboxymethyl hydroxylpropyl guar or combinations thereof.

In some embodiments, the cross-linkable material can be derivatized to include, among other things, small molecules (e.g., tyramine), oligonucleotides or oligopeptides (e.g., polypeptides comprising the Arg-Gly-Asp recognition sequence, also known as "RGD"). The cross-linkable material can be derivatized before it is crosslinked or after it is crosslinked. In some embodiments, the cross-linkable material is derivatized before it is cross-linked.

The cross-linkable material can be crosslinked via any suitable cross-linking mechanism. For example, the cross-linkable material can be crosslinked via covalent crosslinks, non-covalent crosslinks (e.g., with the use of a crosslinking agent) or via a combination of covalent and non-covalent crosslinks.

In some embodiments, the crosslinking agent comprises divalent cations including, but not limited to $Ca^{2+}$, $Mg^{2+}$, $Ba^{2+}$ or combinations thereof. In some embodiments, the crosslinking agent is substantially homogeneously distributed in the microparticles of the embodiments of the present invention.

In some instances it may be advantageous for the divalent cations to be sequestered in any suitable way (e.g., chelation) so that the crosslinking timing and rate can be controlled. For example, in some embodiments, the divalent cations may be chelated with any chelating agent suitable for chelating divalent cations including, but not limited to, ethylenediaminetetraacetic acid (EDTA), ethylene glycol tetraacetic acid (EGTA), cyclohexane diamine tetraacetic acid (CDTA), citrate, and phosphate.

The microparticles of the embodiments of the present invention may be formed by a method comprising forming microdroplets (e.g., microfluidically forming the microdroplets) comprising one or more crosslinkable materials (e.g., linear polysaccharides) and one or more crosslinking agents. In some embodiments, both components, the crosslinkable materials and the crosslinking agents are in liquid form, e.g., as solutions in water or any suitable solvent. The resulting microdroplets can then be contacted with a crosslinking promoter to crosslink the one or more crosslinkable materials (e.g., linear polysaccharides). The crosslinking promoter, in some embodiments, may be a change in the pH, a change in the temperature, a change in the ionic strength or combinations thereof. In some embodiments, the crosslinking promoter is a change in the pH. The change in the pH may be effected with an acid or a base, preferably an acid. In other embodiments, the crosslinking promoter is an ionic species (e.g., in solution) that is different from the crosslinking agent.

The acid may be any suitable acid and the ionic species may be any suitable ionic species, particularly an ionic species having a higher affinity for a chelating agent than the crosslinking agent. The acid and the ionic species cause a sufficient amount of chelated divalent cations to be sufficiently freed from chelation, thereby providing a sufficient amount of unchelated divalent cations to promote crosslinking. Scheme I, below, shows a schematic representation of this process using EDTA as a specific, non-limiting chelating agent and $Ca^{2+}$ as a specific, non-limiting crosslinking agent.

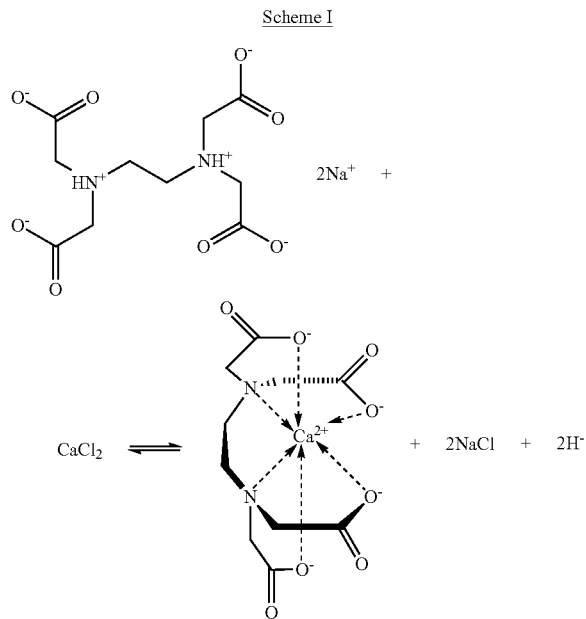

Scheme I

Scheme I shows that there is an equilibrium between the chelated form of $Ca^{2+}$ and the unchelated form of $Ca^{2+}$. The equilibrium may be driven to the left (i.e., to the unchelated form of $Ca^{2+}$) if a proton source (i.e., an acid, crosslinking promoter) is added. Enough acid may be added to generate a proton concentration that is, in turn, sufficient to generate a sufficient concentration of crosslinking agent (e.g., unchelated $Ca^{2+}$) to promote crosslinking.

In a specific, non-limiting example, where the crosslinkable material comprises alginate and the cross-linking agent comprises EDTA-chelated $Ca^{2+}$, above a certain pH, the binding affinity of EDTA for $Ca^{2+}$ is higher than that of alginate. Thus, $Ca^{2+}$ is bound by EDTA and cannot crosslink the alginate. Shifting the pH toward a lower pH decreases the binding strength of EDTA to $Ca^{2+}$. Below a certain pH, the binding strength of alginate is higher than that of EDTA and thus, $Ca^{2+}$ is complexed by alginate and serves as a crosslinking agent. It should be understood, however, that in some instances, depending on the cross-linkable material and/or the cross-linking agent comprising a chelated cation, the affinity of the chelating agent for the cation may be higher at lower pHs and lower at higher pHs, such that crosslinking is substantially prevented at lower pHs and promoted at higher pHs.

In some embodiments, the crosslinking promoter comprises an acid. The acid may be any suitable acid, including HCl and HF. In some embodiments, the acid that may be used as crosslinking promoters includes, but is not limited to, an organic acid. In some embodiments, organic acids include, but are not limited to, carboxylic acids such as $C_2$-$C_{10}$ carboxylic acids (e.g., a $C_2$-$C_8$ carboxylic acid, a $C_2$-$C_5$ carboxylic acid, and a $C_2$-$C_4$ carboxylic acid). Examples of $C_2$-$C_{10}$ carboxylic acids include, but are not limited to acetic acid, formic acid, benzoic acid, citric acid, oxalic acid, lactic acid or combinations thereof.

In some embodiments, the crosslinkable material can comprise functional groups that can be crosslinked via crosslinking mechanisms, in addition to crosslinking via a crosslinking agent. Thus, for example, one of the crosslinking mechanisms can be crosslinking via a crosslinking agent, but there can be at least one other crosslinking mechanism including covalent crosslinking via reactions between alcohols and carboxylic acids to form esters; reactions between amines and carboxylic acids to form amides; reactions between aldehydes and primary amines to form imines that can be reduced to secondary amines, reactions between alcohols and isocyanates to form carbamates; reactions between amines and isocyanates to give ureas; aryl-aryl coupling (e.g., phenol-phenol coupling that is enzymatically catalyzed; see *Journal of Biomedical Materials Research Par A* 85: 345-351 (2008), which is incorporated herein by reference), or combinations thereof. Additional crosslinking mechanism can include radical and photochemical crosslinking mechanisms. In some embodiments, the primary crosslinking mechanism can be crosslinking via a crosslinking agent.

Physical crosslinking mechanisms are also contemplated herein.

The microparticles of the embodiments of the present invention may be used in methods for delivering an active agent to a subject (e.g., a mammal, specifically a human) in need thereof or, in the case of agrochemicals, to an area (e.g., a field or plot) in need thereof. The methods comprise (i) providing or obtaining one or more microparticle comprising an active agent; and (ii) delivering the microparticle to a location (e.g., capillaries, skin, and eye) in a subject in need thereof or a location in an area in need thereof.

The microparticles may be delivered to the subject in need thereof or, in the case of agrochemicals, to an area in need thereof, by any suitable means. Such means for delivering the microparticles of the embodiments of the present invention to a subject in need thereof include, but are not limited to, oral, peroral, parenteral, intravenous, intraperitoneal, intradermal, subcutaneous, intramuscular, nasal, buccal, rectal or topical means, for example on the skin, mucous membranes or in the eyes. Means for delivering or depositing the microparticles of the embodiments of the present invention in an area in need thereof include, but are not limited to, spraying (e.g., an aqueous suspension of the microparticles of the embodiments of the present invention).

In some embodiments, the microparticles of the embodiments of the present invention may be combined with other pharmaceutically acceptable or agronomically acceptable excipients. Such excipients may facilitate the incorporation of the microparticles of the embodiments of the present invention into dosage forms (e.g., capsules, tablets, lozenges, and the like) or into, e.g., pellets for agrochemical applications.

In some embodiments, when the microparticles of the embodiments of the present invention have a liquid core, and the core comprises an active agent, the microparticles can be ruptured by applying a suitable trigger. Such triggers include, but are not limited to mechanical force (e.g., from the hand, when applied to the skin), ultrasound, oxidizing stress, osmotic stress, pH, phototriggers; reducing agents, enzyme/enzymatic triggers, temperature, magnetic fields, and combinations thereof.

In some embodiments, applying oxidizing stress to the microparticles includes contacting the microparticles with or exposing the microparticles to an oxidizing agent. Suitable oxidizing agents include, but are not limited to, silver nitrate, potassium permanganate, sodium periodate, osmium tetroxide, peroxides, and sulfuric acid. An osmotic stress trigger includes, but is not limited to, exposing such microparticles to conditions where the ionic strength outside the microparticles is substantially less than the ionic strength inside the microparticles (i.e., in the core). An example of such a situation includes microparticles containing a high salt (e.g., $CaCl_2$) concentration (e.g., from about 1 to about 2 M salt) in the core being exposed to a significantly lower salt (e.g., about 0 to about 0.5 M) concentration outside the microparticles or vice versa.

In various other embodiments, the invention relates to a system comprising one or more microparticles of the embodiments of the present invention and one or more cells encapsulated in the one or more microparticles. In some embodiments, each microparticle comprises more than one cell. In other embodiments, each microparticle comprises a single cell.

The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those of ordinary skill in the art, and that such modifications and variations are considered to be within the scope of this invention as defined by the appended claims.

EXAMPLES

The present invention can be better understood by reference to the following examples which are offered by way of illustration. The present invention is not limited to the examples given herein.

Example 1

Solid Particles

Using droplet-based microfluidics, monodisperse droplets of a calcium-EDTA/alginate mixture can be produced with a precise size control in the micrometer regime. See FIG. 1, which contains two panels a) and b). Panel a) is a scheme showing the formation of alginate microparticles using a 50 μm PDMS dropmaker (left: channel outline, right: microscopic image of crossjunction (4×)). The liquid microdroplets contain Ca-EDTA (100 mM, pH 7.0)/alginate (2.0% w/v) (1:1). The microdroplets are solidified into microparticles by diffusion of acetic acid present in the outer phase (1.0% PFPE-PEG block-copolymer surfactant (Holtze et al. *Lab Chip* 8: 1632 (2008)) in HFE7500 (3M), and 1 μL/mL acetic acid) into the drop. Panel b) of FIG. 1 shows microscopic images of resulting alginate microparticles. The particle size can be controlled by adapting the flow rates of the system (scale bars 20 nm).

The gels shown in FIG. 1b are produced by using two different dropmakers: the first six images from the left: 25 μm dropmaker, the last six images: 50 μm dropmaker. The flow rate of the inner phase (alginate/EDTA-complex) was kept at 50 μL/h. The flow rate of the oil phase was varied in the following order (from left image to right): 1000, 800, 600, 400, 200, 100 μL/h;

1000, 800, 600, 400, 200, 100 μL/h.

Figure 2:
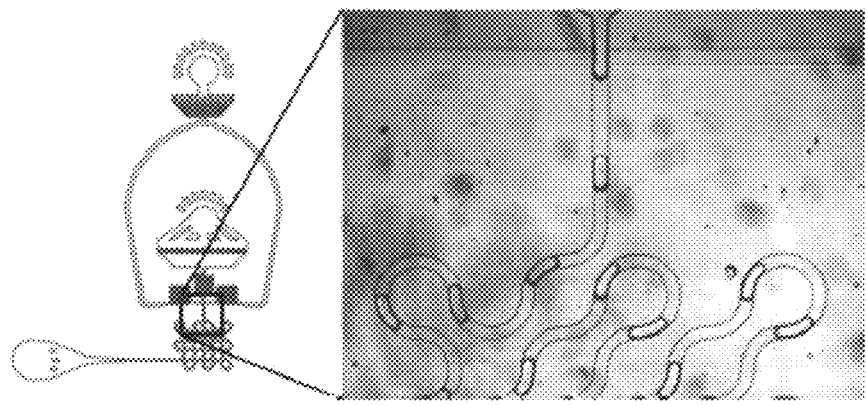
FIG. 2 is a scheme showing the formation of alginate microparticles using a 50 μm PDMS dropmaker with integrated serpentine channel to alter the geometry of the formed microparticles (panel a)); microscopic images of cross-linked alginate microparticles (panel b)); and microscopic images of non-spherical alginate microparticles after transfer into aqueous medium.
Figure 2:
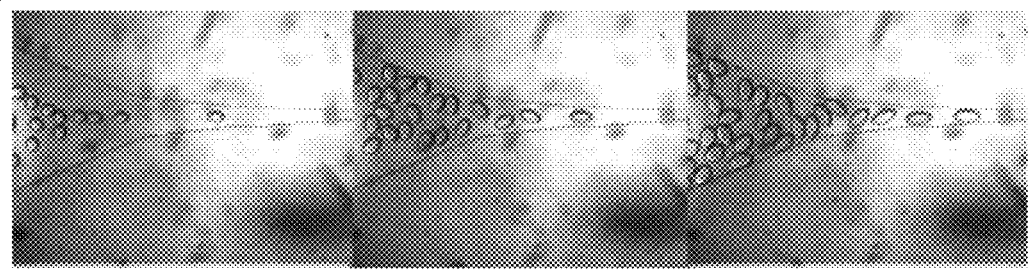
Figure 2:
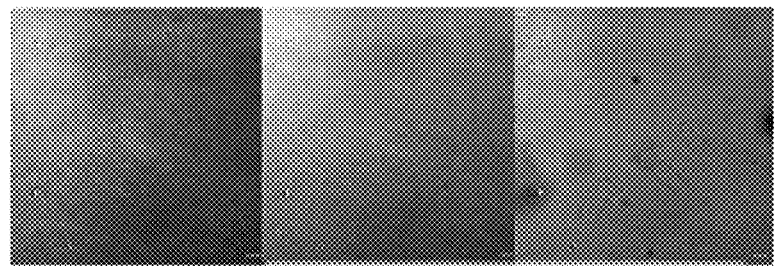

The gelation of the drops can either be induced by diffusion of acetic acid into the drop or by addition of acid-generating compounds into the drops like lactones, specific example is gluconolactone. By controlling the gelation rate, as well as the channel geometry, spherical as well as non-spherical particles are accessible. Rapid gelation of alginate leads to a solidification of the liquid alginate drops inside the microfluidic channel allowing for control over the shape of the cross-linked alginate particles through the design of the channel geometry. Therefore, a variety of non-spherical particles can be created including rods, hooks, crescents, for example. See FIG. 2, which contains three panels a)-c).). Panel a) is a scheme showing the formation of alginate microparticles using a 50 nm PDMS dropmaker (left: channel outline, right: microscopic image of crossjunction (4×)). The liquid microdroplets contain Ca-EDTA (100 mM, pH 7.0)/alginate (2.0% w/v) (1:1). The microdroplets are solidified into microparticles by diffusion of acetic acid present in the outer phase (1.0% PFPE-PEG block-copolymer surfactant (Holtze et al. *Lab Chip* 8: 1632 (2008)) in HFE7500 (3M), and 1 μL/mL acetic acid) into the drop. Panel b) of FIG. 2 shows microscopic images of cross-linked alginate microparticles in the channel outlet (4×). The geometry of the rod-like structure can be influenced by controlling the flow rates during drop formation (flow rates inner/outer phase (in μL/h) from left to right: 50/150, 50/400, 50/800). Panel c) of FIG. 2 shows non-spherical alginate microparticles obtained from different flow rates using the channel geometry shown in panel a) (flow rates inner/outer phase (in μL/h) from left to right: 150/200, 150/500, 150/700) (scale bars 25 μm).

The mechanical properties of the gels can also be controlled by the concentration and chemical nature of the alginates (e.g., molecular weights and β-D-mannuronate (M)/α-L-guluronate (G) ratios/lengths). To enhance the stability of the microparticles, a combination of physical and chemical cross-linking can be performed by the incorporation of covalently cross-linkable groups, e.g., phenol units. See, e.g., *Journal of Biomedical Materials Research Par A* 85: 345-351 (2008), which is incorporated by reference.

The developed approach is compatible with microfluidic methods and drop formation techniques and can be combined with a variety of microfluidic applications as cell encapsulation, high-throughput analysis or materials production.

Example 2

Cell-Encapsulation

Cell-containing microparticles can be generated by combining the described method with microfluidic cell encapsulation techniques. See Clausell-Tormos et al. *Chemistry & Biology* 15: 427 (2008) and Koster et al. *Lab Chip* 8: 1110 (2008). After gelation the resulting cell-laden microparticles can be transferred into aqueous cell culture medium without losing the integrity of the generated microenvironment. Any surfactant present when the microparticles are formed may be removed by addition of a suitable agent such as perfluoro-1-octanol (PFO), followed by subsequent centrifugation, removal of the oil phase, and re-dispersion of the microparticles in cell culture medium.

Figure 3:
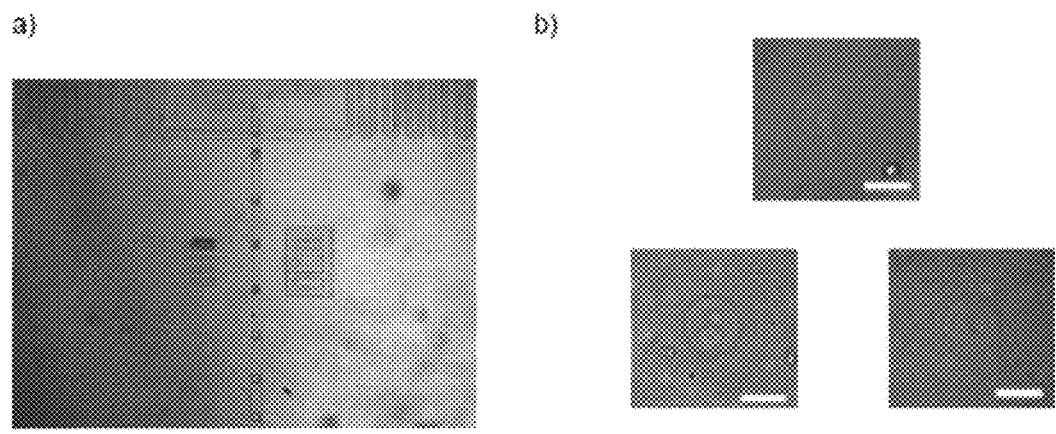
FIG. 3 is microscopic images of a 25 micrometer dropmaker (panel a)); and microscopic images of the resulting cell-containing microgels (panel b)) after breaking the emulsion with perfluoro-1-octanol (PFO).

Single, as well as multiple biological entities, e.g., mammalian and plant cells, proteins or peptides (e.g., collagen, RGD, antibodies), bacteria, viruses, can be incorporated into one microparticles of the embodiments of the present invention allowing for long-term biological screenings, single-cell analysis, and culturing in independent microenvironments. See FIG. 3, which contains two panels a) and b). Panel a) shows microscopic images of a 25 micrometer dropmaker (inner phase: Ca-EDTA (100 mM, pH 7.0)/alginate (2.0% w/v) (1:1); outer phase: 1.0% PFPE-PEG block-copolymer surfactant (Holtze et al. *Lab Chip* 8: 1632 (2008)) in HFE7500 (3M), and 1 µL/mL acetic acid) (4×). Panel b) in FIG. 3 is microscopic images of the resulting cell-containing microgels (carrying single or multiple cells) after breaking the emulsion with PFO, centrifugation, and transfer to aqueous medium (scale bars: 25 micrometer).

The solid nature of the microparticle can also be used as scaffold or solid-support for adherent cells and thus mimics conditions found in vivo or in bulk cell culture experiments.

The encapsulated cells show good viability and proliferation for several weeks. In analogy to experiments with liquid cell-laden drops, the cell-containing microparticles can individually be manipulated (sorting, screening, picoinjection, etc.). See Schmitz et al., *Lab Chip* 9: 44 (2009); Abate et al., *PNAS* 107: 19163 (2010); Agresti et al., *PNAS* 107: 4004 (2010); Baret, *Lab Chip* 9: 1850 (2009); and Guo et al., *Lab Chip* 12: 2146 (2012).

Concerning long-term cell culture, a homogeneous gelation which is directly correlated with the mechanical properties of the corresponding gel may impact acceptable experimental reproducibility. It has been shown that the proliferation of cells may be influenced by the mechanical properties of their environment and is therefore mechanical properties is an important factor for screening and cell culture applications. See Klein et al., *Current Biology* 19: 1511 (2009); and Khatiwala et al., *Am. J. Physiol. Cell Physiol.* 290: C1640 (2006).

Example 3

Core-Shell Particles and Capsules

Figure 4:
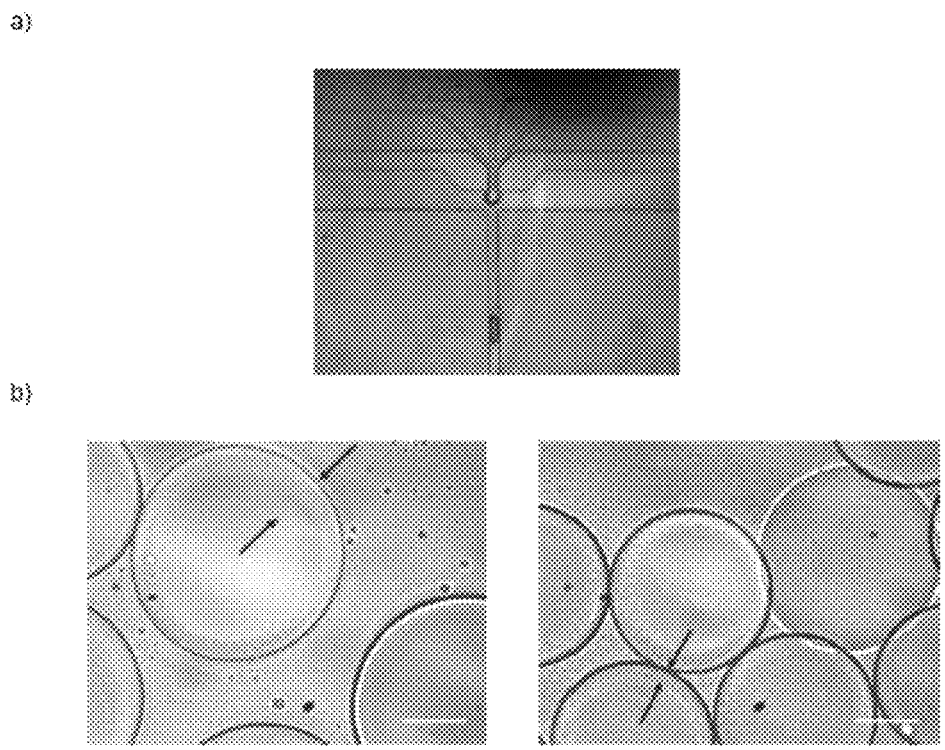
FIG. 4 is microscopic images showing the formation of a water in water in oil (w/w/o) double emulsion using a two-dimensional microfluidic PDMS device (panel a)); and microscopic images of resulting microparticles with different alginate shell thicknesses (panel b)).

Core-shell geometries and capsules can be assembled as any suitable emulsion, including, but not limited to, water-in-water-in-oil (w/w/o), o/w/o, and w/o/w double emulsions. See FIG. 4, which contains two panels a) and b). Panel a) is microscopic images showing the formation of a water in water in oil (w/w/o) double emulsion using a two-dimensional microfluidic PDMS device (inner phase: 20% PEG, middle phase: Ca-EDTA (100 mM, pH 7.0)/alginate (2% w/v) (1:1), outer phase: 1.0% PFPE-PEG block-copolymer surfactant (Holtze et al. *Lab Chip* 8: 1632 (2008)) in HFE7500 (3M), and 1 µL/mL acetic acid (4×)). The Ca-EDTA/alginate shell is solidified by diffusion of acetic acid present in the outer phase into the drop. Panel b) of FIG. 4 is microscopic images of resulting alginate microparticles with different shell thicknesses (not density matched) obtained by different flow rates (flow rates inner/middle/outer phase (in µL/h) from left to right: 20/60/1000, 60/20/1000) (scale bars: 25 µm).

If alginate is used as an outer phase, homogenous capsules can be assembled and their size and shell thickness can be tuned with the flow rates and device geometry. In analogy to the solid particles described in Example 1, the microparticles can be transferred into aqueous media after alginate is gelled.

For w/w/o emulsions alginate forms the middle phase and the oil phase forms the outer phase.

Core-shell particles of a great variety of materials can be formed by changing the composition of the inner phase. For example, the use of alginate solutions of different concentrations, properties, and/or compositions (e.g., molecular weights, M/G-ratios, ratio of concentration of alginate to $Ca^{2+}$, and any additional degree of crosslinking, in cases where the alginte has been, e.g., covalently crosslinked to some/any extent) lead to alginate/alginate core-shell particles exhibiting a gradient in stiffness. Thus, for example, a lower molecular weight alginate will result in a "softer" microparticle. Also, when gels are made from an alginate rich in guluronic acid residues, higher moduli are obtained compared to gels made from alginates less enriched in G residues. While not being bound by any particular theory, it is believed that the reason for this behavior is that high-G gels, with their long G-blocks and their short elastic segments become more of a stiff open and static network compared to the more dynamic and entangled network structure of the low-G gels with their relative long elastic segments. See *Inter. J. Biol. Macromol.* 21: 47-55 (1997).

In analogy to alginate hydrogel drops, cells can also be loaded into these capsules and core-shell particles.

Additionally, the formation of shells thicknesses in the nanometer range as well as the generation of water in water in water (w/w/w) emulsions may be possible. Triple or higher order emulsions are also possible.

Example 4

Figure 5:
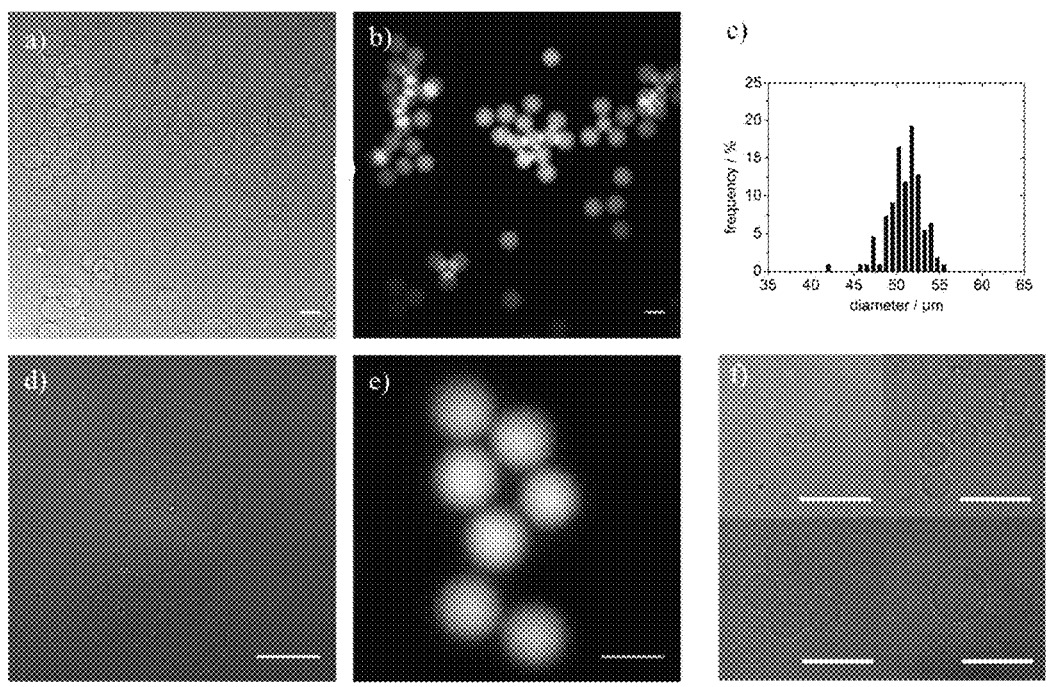
FIG. 5 is bright-field images (panels a) and d)) and fluorescent images (panel b) and e)) of alginate microparticles after transfer into an aqueous medium; and a plot of diameter vs. frequency (panel c)).

FIG. 5 contains bright-field (panels a)) and fluorescent (panel b)) images of alginate microparticles after transfer into an aqueous medium. The images reflect the high monodispersity of the spherical particles as shown in panel c). The high-magnification images (panel d)=bright-field; and panel e)=fluorescent) reveals the homogeneous structure of the alginate microsphere. Panel f) contains bright-field images of homogeneous alginate microgels with 15, 21, 28 and 39 µm in diameter. All scale bars are 50 µm.

Example 5

Figure 6:
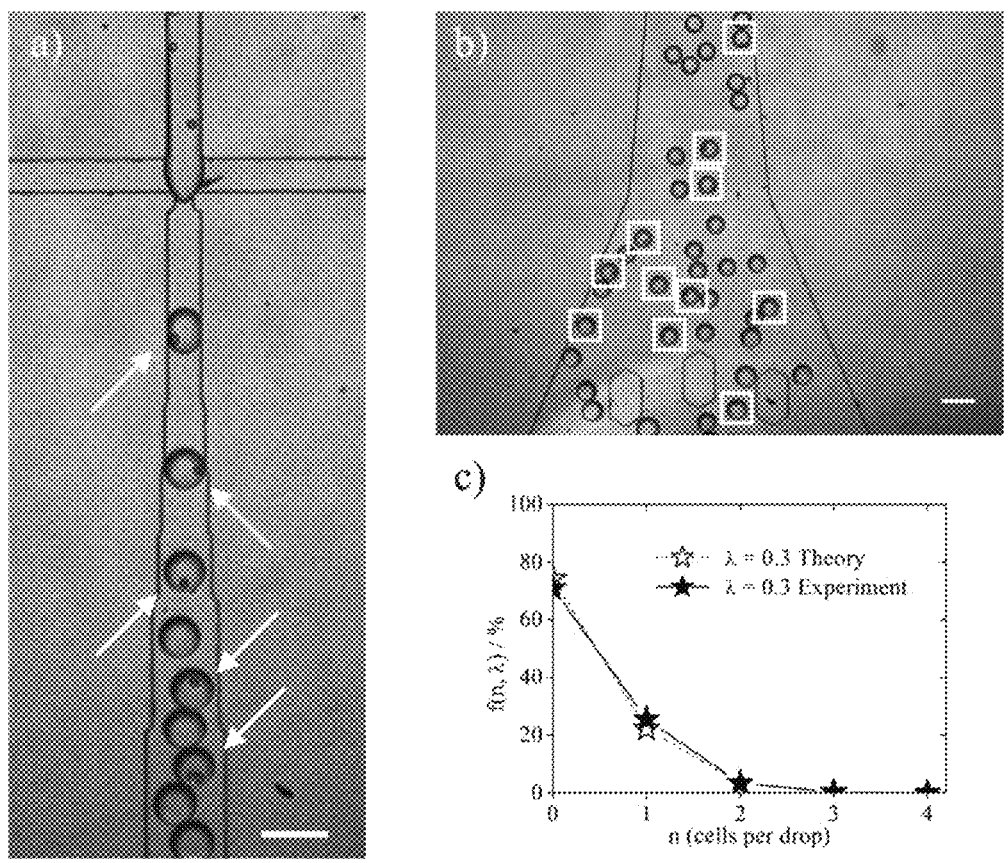
FIG. 6 is microscopic images of cell-laden microgels formed using a 50 micrometer dropmaker (panels a) and b)); and a plot showing a Poisson distribution resulting in approximately 22% of single-cell containing droplets (panel c)).

Cell-laden microgels were formed using a 50 micrometer dropmaker. See FIG. 6 panel a). During the drop formation process, cells are encapsulated and the resulting microgels are collected at the channel outlet. See FIG. 6, panel b). Single-cell containing droplets are indicated by white arrows and boxes in panels a) and b), respectively. The encapsulation process follows the Poisson distribution resulting in approximately 22% of single-cell containing droplets. See panel c). All scale bars are 100 µm.

Example 6

Figure 7:
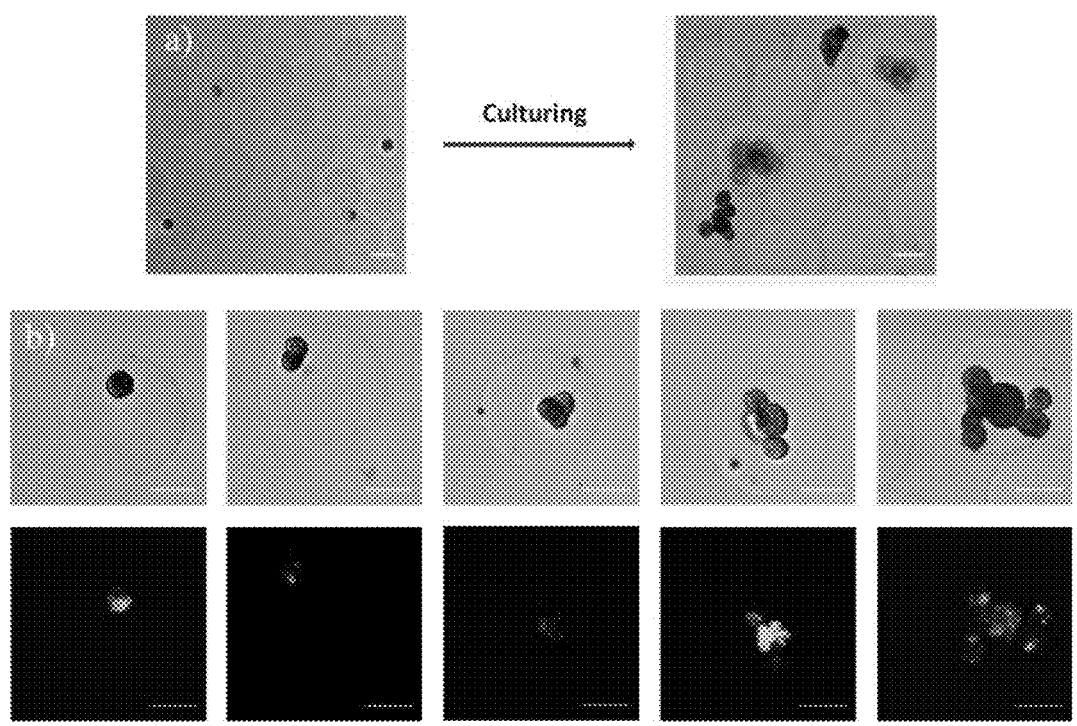
FIG. 7 is microscopic images of proliferating cells inside individual alginate microparticles during culturing over the course of three weeks after addition of a live-stain (panels a)-c)). Living cells show a bright green fluorescence.

Cell-containing microparticles were observed directly after encapsulation and during culture over the period of 366 h. See FIG. 7, panel a). Representative images of proliferating cells inside individual alginate microparticles after addition of a live stain. See FIG. 7, panel b). Living cells exhibit green fluorescence. See FIG. 7, panel b), lower row. About 80% of the cells were alive directly after encapsulation and transfer into cell culture medium. The cells show a natural proliferation inside the droplets under maintenance of their spherical shape. After three weeks of encapsulation the cell viability was determined to be 55%. All scale bars are 25 µm.

Example 7

Binary Microparticles

Figure 8:
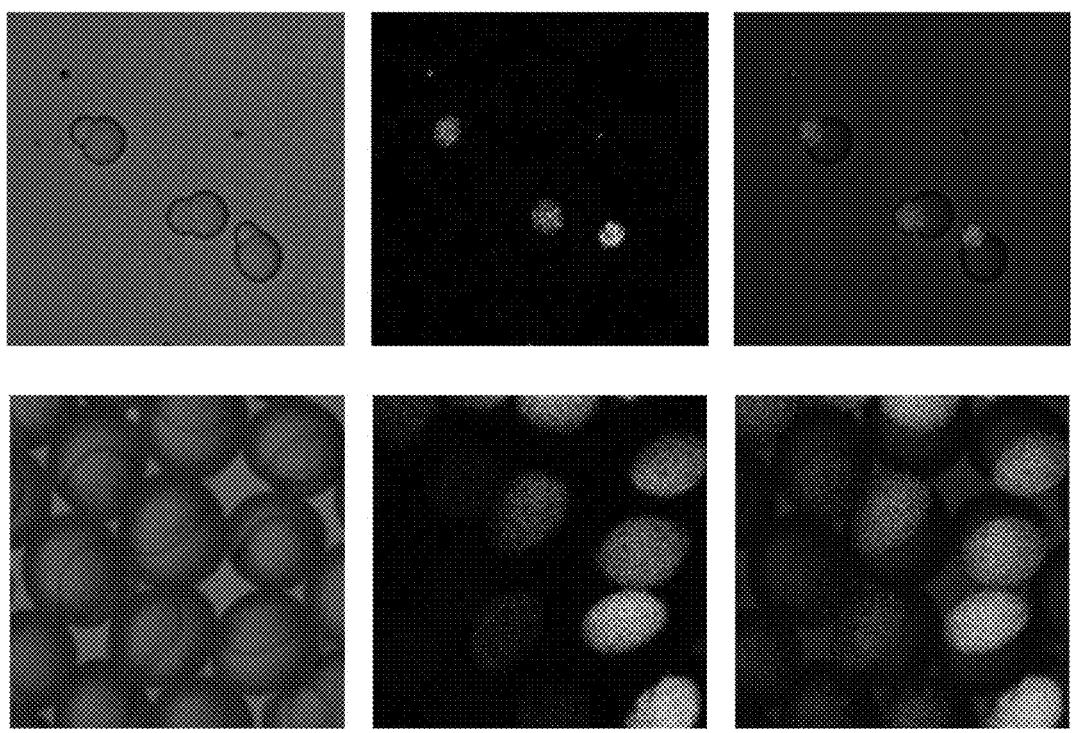
FIG. 8 is microscopic images of "Janus-type" binary microparticles. A fluorescently labeled alginate was used to identify the alginate-rich regions of the binary particle.

In some embodiments, the microparticles can be "Janus-type" binary microparticles, where the microparticle is divided into two separate regions that may be made of the same material. In some embodiments, the microparticle is divided into two separate regions (e.g., compartments) that may be made of a different material. See, e.g., FIG. 8. For example, in some embodiments, the two separate regions can contain two compartments, each compartment comprising different materials where one compartment can comprise a single or a plurality of suitable magnetic nanoparticles (e.g., iron oxide nanoparticles) and the other compartment can comprise no magnetic nanoparticles. And in embodiments where the two separate regions contain two compartments, each compartment comprising the same material, both compartments can comprise a single or a plurality of suitable magnetic nanoparticles (e.g., iron oxide nanoparticles).

In other embodiments, each compartment can comprise at least one cell, where the cell or cells in each compartment can be the same or the cell or cells in a first compartment is different from the cell or cells in a second compartment. Even if the at least one cell is the same in each compartment, the at least one active agent may be present at a different cell concentration in each compartment. Or if the at least one cell is different in each compartment, the two different at least one cells may also be present at a different cell concentration.

In other embodiments, each compartment can comprise at least one active agent, where the active agent or agents in each compartment can be the same or the active agent or agents in a first compartment is different from the active agent or agents in a second compartment. Even if the at least one active agent is the same in each compartment, the at least one active agent may be present at a different concentration in each compartment. Or if the at least one active agent is different in each compartment, the two different at least one active agents may also be present at a different concentration.

In some embodiments, binary microparticles may be prepared microfluidically using the same microfluidic apparatus used to make core-shell microparticles herein by mismatching the osmotic pressure in the inner phase (e.g., a PEG phase) and the middle phase (e.g., an alginate-containing phase) in a w/w/o double emulsion. A solution containing an EDTA-calcium complex is added to the alginate phase but not to the inner phase. After polymerization of the alginate phase, the core-shell microparticle phase-separate into two distinct domains. Ternary and higher order particle architectures can also be envisioned.

The present invention provides for the following exemplary embodiments, the numbering of which is not to be construed as designating levels of importance:

Embodiment 1 relates to microparticles comprising: a cross-linked gel; wherein the microparticles have a coefficient of variation in the size distribution of the microparticles of from about 0.03 to about 0.05 and wherein the microparticles have at least one dimension measuring from about 5 μm to about 200 μm.

Embodiment 2 relates to the microparticles of Embodiment 1, wherein the crosslinked gel comprises one or more crosslinked linear polysaccharides.

Embodiment 3 relates to the microparticles of Embodiment 2, wherein the crosslinked linear polysaccharide comprises alginate, chitosan, curdlan, dextran, emulsan, a galactoglucopolysaccharide, gellan, glucuronan, N-acetyl-heparosan, hyaluronic acid, indicant, kefiran, lentinan, levan, mauran, pullulan, scleroglucan, schizophyllan, stewartan, succinoglycan, xanthan, xylane, welan, starch, tamarind, tragacanth, guar gum, derivatized guar, gum ghatti, gum arabic, locust bean gum, cellulose, hemicellulose, carboxymethyl cellulose, hydroxyethyl cellulose, carboxymethyl hydroxyethyl cellulose, hydroxypropyl cellulose, methyl hydroxyl ethyl cellulose, guar, hydroxypropyl guar, carboxy methyl guar, carboxymethyl hydroxylpropyl guar or combinations thereof.

Embodiment 4 relates to the microparticles of Embodiment 2, wherein the crosslinked linear polysaccharide comprises crosslinked alginate.

Embodiment 5 relates to the microparticles of Embodiment 2, wherein the crosslinked linear polysaccharide comprises a crosslinking agent.

Embodiment 5A relates to the microparticles of Embodiment 5, wherein the crosslinking agent is substantially homogenously distributed in the microparticle.

Embodiment 5B relates to the microparticles of Embodiment 5, wherein the microparticles are core-shell microparticles or binary or higher order microparticles; and the crosslinking agent is substantially homogenously distributed in the core, the shell, or the core and the shell of core-shell microparticles; or, when the microparticles are binary or higher order microparticles, in one or more (preferably all) of the microparticles comprised in the binary or higher order microparticles.

Embodiment 6 relates to the microparticles of Embodiment 5, wherein the crosslinking agent comprises divalent cations.

Embodiment 7 relates to the microparticles of Embodiment 6, wherein the divalent cations comprise $Ca^{2+}$, $Mg^{2+}$, $Ba^{2+}$ or combinations thereof.

Embodiment 8 relates to the microparticles of Embodiments 1-7, wherein the microparticles are substantially spherical.

Embodiment 9 relates to the microparticles of Embodiments 1-7, wherein the microparticles are rod-, crescent- or hook-shaped.

Embodiment 10 relates to the microparticles of Embodiments 8 or 9, wherein the microparticles are core-shell microparticles.

Embodiment 11 relates to the microparticles of Embodiments 8 or 9, wherein the microparticles are binary microparticles.

Embodiment 12 relates to the microparticles of Embodiment 10, wherein the core is a liquid core, a solid core or a gas core.

Embodiment 13 relates to the microparticles of Embodiment 12, wherein the core is an aqueous core.

Embodiment 14 relates to the microparticles of Embodiment 10, wherein the microparticles comprise a liquid core and a solid shell; a gas core and a solid shell; or a solid core and a solid shell.

Embodiment 15 relates to the microparticles of Embodiment 10, wherein the core and/or the shell comprises one or more cells. In another embodiment, at least one of the core and the shell comprises one or more cells.

Embodiment 16 relates to the microparticles of Embodiments 1-5, 5A, 5B, and 6-15, wherein the microparticles comprise an active agent.

Embodiment 17 relates to the microparticles of Embodiment 16, wherein the active agent is a pharmaceutical, an agrochemical or a food additive.

Embodiment 18 relates to the microparticles of Embodiments 1-5, 5A, 5B, and 6-17, wherein the microparticles are degradable, non-degradable or partially degradable.

Embodiment 19 relates to the microparticles of Embodiments 1-5, 5A, 5B, and 6-18, wherein the microparticles comprise pores.

Embodiment 20 relates to microparticles comprising: a $Ca^{2+}$-cross-linked alginate gel; wherein the microparticles have a coefficient of variation in the size distribution of the microparticles of from about 0.03 to about 0.05 and wherein the microparticles have at least one dimension measuring from about 5 µm to about 200 µm.

Embodiment 21 relates to a method of forming the microparticles of Embodiment 1, the method comprising: forming microdroplets comprising one or more crosslinkable linear polysaccharides and one or more crosslinking agents; contacting the microdroplets with a crosslinking promoter to promote crosslinking of the one or more crosslinkable linear polysaccharides.

Embodiment 22 relates to the method of Embodiment 21, wherein the crosslinking agent does not substantially crosslink the one or more crosslinkable linear polysaccharides in an initial state, but, upon contacting with the crosslinking promoter, crosslinks the one or more crosslinkable linear polysaccharides in a second state.

Embodiment 23 relates to the method of Embodiment 22, wherein the first state comprises a sequestered state of the one or more crosslinking agents and the second state comprises an unsequestered state of the one or more crosslinking agents.

Embodiment 24 relates to the method of Embodiments 21-23, wherein the crosslinking agent is substantially homogenously distributed in the microparticle.

Embodiment 25 relates to the method of Embodiment 21-24, wherein said forming comprises microfluidically forming the microdroplets.

Embodiment 26 relates to the method of Embodiment 21-25, wherein the crosslinking agent comprises divalent cations.

Embodiment 27 relates to the method of Embodiment 26, wherein the divalent cations comprise $Ca^{2+}$, $Mg^{2+}$, $Ba^{2+}$ or combinations thereof.

Embodiment 28 relates to the method of Embodiment 26, wherein the divalent cations are sequestered.

Emodiment 29 relates to the method of Embodiment 28, wherein the sequestered divalent cations are chelated.

Embodiment 30 relates to the method of Embodiment 29, wherein the chelated divalent cations comprise $Ca^{2+}$-EDTA.

Embodiment 31 relates to the method of Embodiments 21-30, wherein said crosslinking promoter comprises a change in the pH, a change in the temperature, a change in the ionic strength or combinations thereof.

Embodiment 32 relates to the method of Embodiment 31, wherein said crosslinking promoter comprises a change in the pH.

Embodiment 33 relates to the method of Embodiment 32, wherein the change in the pH is effected with an acid.

Embodiment 34 relates to the method of Embodiment 33, wherein the acid comprises a carboxylic acid.

Embodiment 35 relates to the method of Embodiment 34, wherein the carboxylic acid comprises a $C_2$-$C_{10}$-carboxylic acid.

Embodiment 36 relates to the method of Embodiment 35, wherein the $C_2$-$C_{10}$-carboxylic acid comprises acetic acid, formic acid, benzoic acid, citric acid, oxalic acid, lactic acid or combinations thereof.

Embodiment 37 relates to the method of Embodiment 36, wherein the divalent cations are sequestered and the crosslinking promoter causes sequestered divalent cations to be sufficiently freed from sequestration such that crosslinking of the one or more crosslinkable linear polysaccharides is promoted.

Embodiment 38 relates to a method of forming the microparticles of Embodiment 20, the method comprising: forming microdroplets comprising alginate and $Ca^2$-EDTA; and contacting the microdroplets with a crosslinking promoter to promote crosslinking of the alginate.

Embodiment 39 relates to a method for delivering one or more microparticles of Embodiments 1-5, 5A, 5B, and 6-20, or microparticles made according to the method of Embodiments 21-38, to a location in a subject in need thereof or to an area in need thereof, the method comprising (i) providing or obtaining one or more microparticle comprising an active agent; and (ii) delivering the microparticle to a location in a subject in need thereof or a location in an area in need thereof.

Embodiment 40 relates to a system comprising one or more microparticles of Embodiments 1-5, 5A, 5B, and 6-20, or microparticles made according to the method of Embodiments 21-38, and one or more cells encapsulated in the one or more microparticles of Embodiments 1-5, 5A, 5B, and 6-20, or microparticles made according to the method of Embodiments 21-38.

Embodiment 41 relates to the use of the microparticles of Embodiments 1-5, 5A, 5B, and 6-20, or microparticles made according to the method of Embodiments 21-38, in pharmaceuticals, medical, biotechnology, cosmetics, food additives, optical devices, sensors or combinations thereof.

Embodiment 42 relates to the microparticles Embodiments 1-5, 5A, 5B, and 6-19, wherein the microparticles comprise magnetic nanoparticles.

What is claimed is:

1. A method of forming microparticles, comprising:
    passing a plurality of microdroplets comprising a gel precursor through a curved microfluidic channel having at least one dimension measuring from about 5 µm to about 200 µm; and
    crosslinking the gel precursor to form a plurality of microparticles comprising a crosslinked gel, the microparticles having a shape conforming to the shape of the curved microfluidic channel.

2. The method of claim 1, wherein the microparticles have a coefficient of variation in size distribution of from about 0.03 to about 0.05.

3. The method of claim 1, wherein the microparticles are crescent- or hook-shaped.

4. The method of claim 1, wherein crosslinking the gel precursor to form a plurality of microparticles comprises microfluidically forming the microdroplets.

5. The method of claim 1, wherein the gel precursor comprises one or more crosslinkable linear polysaccharides and one or more crosslinking agents.

6. The method of claim 5, comprising crosslinking the gel precursor with a crosslinking promoter to promote crosslinking of the one or more crosslinkable linear polysaccharides.

7. The method of claim 6, wherein the crosslinking agent does not substantially crosslink the one or more crosslinkable linear polysaccharides in an initial state, but upon contacting with the crosslinking promoter, crosslinks the one or more crosslinkable linear polysaccharides in a second state.

8. The method of claim 7, wherein the initial state comprises a sequestered state of the one or more crosslinking agents and the second state comprises an unsequestered state of the one or more crosslinking agents.

9. The method of claim 6, wherein said crosslinking promoter comprises a change in pH, a change in temperature, a change in ionic strength or combinations thereof.

10. The method of claim 9, wherein said crosslinking promoter comprises a change in the pH.

11. The method of claim 10, wherein the change in the pH is effected with an acid.

12. The method of claim 6, wherein the crosslinking agent comprises divalent cations.

13. The method of claim 12, wherein the divalent cations are sequestered.

14. The method of claim 13, wherein the sequestered divalent cations are chelated.

15. The method of claim 14, wherein the chelated divalent cations comprise $Ca^{2+}$-EDTA.

16. The method of claim 12, wherein the divalent cations are sequestered and the crosslinking promoter causes the sequestered divalent cations to be sufficiently freed from sequestration such that crosslinking of the one or more crosslinkable linear polysaccharides is promoted.

\* \* \* \* \*